(12) United States Patent
Cork et al.

(10) Patent No.: US 7,773,790 B2
(45) Date of Patent: *Aug. 10, 2010

(54) METHOD FOR DETECTING THE PRESENCE OF A TARGET ANALYTE IN A TEST SPOT

(75) Inventors: William Cork, Lake Bluff, IL (US); Tim Patno, Chicago, IL (US); Mark Weber, Cary, IL (US); Dave Morrow, Chicago, IL (US); Wesley Buckingham, Chicago, IL (US)

(73) Assignee: Nanosphere, Inc., Northbrook, IL (US)

( * ) Notice: Subject to any disclaimer, the term of this patent is extended or adjusted under 35 U.S.C. 154(b) by 1006 days.

This patent is subject to a terminal disclaimer.

(21) Appl. No.: 11/530,110

(22) Filed: Sep. 8, 2006

(65) Prior Publication Data

US 2007/0041624 A1      Feb. 22, 2007

Related U.S. Application Data

(62) Division of application No. 10/210,959, filed on Aug. 2, 2002, now Pat. No. 7,110,585.

(60) Provisional application No. 60/310,102, filed on Aug. 3, 2001, provisional application No. 60/366,732, filed on Mar. 22, 2002.

(51) Int. Cl.
*G06K 9/00* (2006.01)

(52) U.S. Cl. .................. 382/128; 382/129; 382/130; 382/133; 382/134

(58) Field of Classification Search ............... 382/128, 382/129, 130, 133, 134, 141–145, 149; 348/125, 348/126, 128
See application file for complete search history.

(56) References Cited

U.S. PATENT DOCUMENTS 4,202,037 A     5/1980     Glaser et al.

(Continued)

FOREIGN PATENT DOCUMENTS

WO     WO 98/44330     10/1998

(Continued)

OTHER PUBLICATIONS

Sonnichsen, C. et al., "Spectroscopy of single metallic nanoparticles using total internal reflection microscopy", Applied Physics Letters, vol. 77, No. 19, 2000, pp. 2949-2951.

(Continued)

*Primary Examiner*—Brian Q Le
(74) *Attorney, Agent, or Firm*—Gregory T. Pletta

(57) ABSTRACT

An apparatus and method for imaging metallic nanoparticles is provided. Preferably, the invention provides for an apparatus and method for detection of gold colloid particles and for accurate reporting to the operator. The apparatus includes a substrate holder for holding the substrate, a processor and memory device, an imaging module, an illumination module, a power module, an input module, and an output module. The apparatus may have a stationary substrate holder and imaging module which are proximate to one another. The apparatus provided for a compact sized system without the need for complex motorized devices to move the camera across the substrate. Further, the apparatus and method provide for automatic detection of the spots/wells on the substrate, automatic quantification of the spots on the substrate, and automatic interpretation of the spots based on decision statistics.

6 Claims, 26 Drawing Sheets

U.S. PATENT DOCUMENTS

| | | |
|---|---|---|
| 5,018,219 A | 5/1991 | Matsuzaki et al. |
| 5,428,690 A | 6/1995 | Bacus et al. |
| 5,599,668 A | 2/1997 | Stimpson et al. |
| 6,143,247 A | 11/2000 | Sheppard, Jr. et al. |
| 6,212,292 B1 | 4/2001 | Soares |
| 6,214,560 B1 | 4/2001 | Yguerabide et al. |
| 6,248,988 B1 | 6/2001 | Krantz |
| 6,268,218 B1 | 7/2001 | Pantoliano et al. |
| 6,286,763 B1 | 9/2001 | Reynolds et al. |
| 6,396,941 B1 | 5/2002 | Bacus et al. |
| 6,649,403 B1 | 11/2003 | McDevitt et al. |
| 6,728,417 B1 | 4/2004 | Hara et al. |
| 7,321,829 B2 | 1/2008 | Remacle et al. |
| 2003/0095764 A1 | 5/2003 | Pering et al. |
| 2003/0224505 A1 | 12/2003 | Patno et al. |
| 2004/0014106 A1 | 1/2004 | Patno et al. |

FOREIGN PATENT DOCUMENTS

| | | |
|---|---|---|
| WO | WO 99/13319 | 3/1999 |
| WO | WO 02/086468 | 10/2002 |
| WO | WO 03/053535 | 7/2003 |
| WO | WO 03/060446 | 7/2003 |

OTHER PUBLICATIONS

Storhoff, J. et al., "Homogeneous detection of unamplified genomic DNA sequences based on colorimetric scatter of gold nanoparticle probes", Nature Biotechnology, vol. 22, No. 7, 2004, pp. 883-887.

Storhoff, J. et al., "Gold nanoparticle-based detection of genomic DNA targets on microarrays using a novel optical detection system", Biosensors & Bioelectronics, vol. 19, 2004, pp. 875-883.

Taton, T. et al., "Scanometric DNA Array Detection with Nanoparticle Probes", Science, vol. 289, 2000, pp. 1757-1760.

Alexandre, I. et al., "Colorimetric Silver Detection of DNA Microarrays", Analytical Biochemistry, vol. 295, No. 1, 2001, pp. 1-8.

Brown, C.S., et al., "Image metrics in the statistical analysis of DNA microarray data," Proceedings of the National Academy of Sciences of USA, National Academy of Science, Washington D.C., US, vol. 98, No. 16, Jul. 31, 2001, pp. 8944-8949.

Takahagi, T., et al., "Scanning Electron Microscope Observation of Heterogeneous Three-Dimensional Nanoparticle Arrays Using DNA," Japanese Journal of Applied Physics, Japan Society of Applied Physics, Tokyo, Japan, vol. 40, No. 5B, Part 2, May 15, 2001. pp. L521-.

Supplementary European Search Report for related European Patent Application No. EP 02 80 5501, Nov. 8, 2005.

International Search Report for related PCT Application No. PCT/US02/24604, Aug. 25, 2003.

International Search Report for related PCT Application No. PCT/US2005/001011, Jun. 14, 2005.

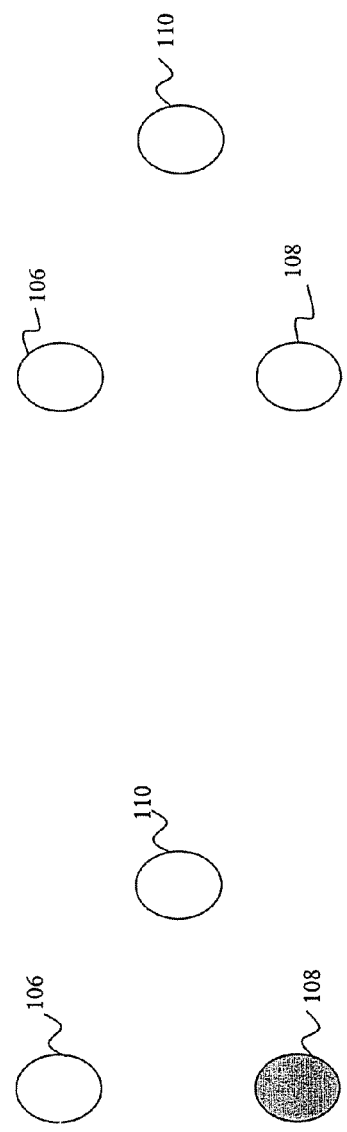
FIG. 16a
FIG. 16b
FIG. 16c
FIG. 16d

METHOD FOR DETECTING THE PRESENCE OF A TARGET ANALYTE IN A TEST SPOT

REFERENCE TO RELATED APPLICATIONS

This application is a divisional application of U.S. patent application Ser. No. 10/210,959, filed on Aug. 2, 2002 and entitled "Nanoparticle Imaging System and Method," now U.S. Pat. No. 7,110,585, which claims the benefit of both U.S. Patent Application Ser. No. 60/310,102 filed on Aug. 3, 2001 and entitled "Nanoparticle Imaging System and Method," and U.S. Patent Application Ser. No. 60/366,732 filed on Mar. 22, 2002 and entitled "Method and System for Detecting Nanoparticles." This application incorporates by reference U.S. Patent Application Ser. No. 60/366,732 in its entirety, U.S. Patent Application Ser. No. 60/310,102 in its entirety, and U.S. patent application Ser. No. 10/210,959 in its entirety.

FIELD OF THE INVENTION

This present invention relates to detection of metallic nanoparticles. More specifically, the invention provides for methods and apparatuses for detection of gold colloid particles and for accurate reporting to the operator.

BACKGROUND OF THE INVENTION

Sequence-selective DNA detection has become increasingly important as scientists unravel the genetic basis of disease and use this new information to improve medical diagnosis and treatment. DNA hybridization tests on oligonucleotide-modified substrates are commonly used to detect the presence of specific DNA sequences in solution. The developing promise of combinatorial DNA arrays for probing genetic information illustrates the importance of these heterogeneous sequence assays to future science.

Typically, the samples are placed on or in a substrate material that facilitates the hybridization test. These materials can be glass or polymer microscope slides or glass or polymer microtiter plates. In most assays, the hybridization of fluorophore-labeled targets to surface bound probes is monitored by fluorescence microscopy or densitometry. However, fluorescence detection is limited by the expense of the experimental equipment and by background emissions from most common substrates. In addition, the selectivity of labeled oligonucleotide targets for perfectly complementary probes over those with single base mismatches can be poor, limiting the use of surface hybridization tests for detection of single nucleotide polymorphisms. A detection scheme which improves upon the simplicity, sensitivity and selectivity of fluorescent methods could allow the full potential of combinatorial sequence analysis to be realized.

One such technique is the chip based DNA detection method that employs probes. A probe may use synthetic strands of DNA complementary to specific targets. Attached to the synthetic strands of DNA is a signal mechanism. If the signal is present (i.e., there is a presence of the signal mechanism), then the synthetic strand has bound to DNA in the sample so that one may conclude that the target DNA is in the sample. Likewise, the absence of the signal results (i.e., there is no presence of the signal mechanism) indicates that no target DNA is present in the sample. Thus, a system is needed to reliably detect the signal and accurately report the results.

One example of a signal mechanism is a gold nanoparticle probe with a relatively small diameter (10 to 40 nm), modified with oligonucleotides, to indicate the presence of a particular DNA sequence hybridized on a substrate in a three component sandwich assay format. See U.S. Pat. No. 6,361,944 entitled "Nanoparticles having oligonucleotides attached thereto and uses therefore," herein incorporated by reference in its entirety; see also T. A. Taton, C. A. Mirkin, R. L. Letsinger, *Science*, 289, 1757 (2000). The selectivity of these hybridized nanoparticle probes for complementary over mismatched DNA sequences was intrinsically higher than that of fluorophore-labeled probes due to the uniquely sharp dissociation (or "melting") of the nanoparticles from the surface of the array. In addition, enlarging the array-bound nanoparticles by gold-promoted reduction of silver(I) permitted the arrays to be imaged in black-and-white by a flatbed scanner with greater sensitivity than typically observed by confocal fluorescent imaging of fluorescently labeled gene chips. The scanometric method was successfully applied to DNA mismatch identification.

However, current systems and methods suffer from several deficiencies in terms of complexity, reliably detecting the signal and accurately reporting the results. Prior art systems often times include large optics packages. For example, a typical imaging system may have a camera which is over 2½ feet from the object plane (where the specimen sits). This large distance between the camera and the object plane results in a very large imaging device. Unfortunately, a large imaging system may occupy a significant portion of limited space within a laboratory. In order to meet this compact size requirement, other prior art imaging devices have reduced the distance between the camera and the object plane. While this reduces the size of the system, the small distance between the camera and the object plane can cause a great amount of distortion in the image acquired, with little distortion occurring at the center of the lens and with great distortion occurring around the outer portions of the image acquired. In order to avoid significant distortion and to increase the resolution in the acquired image, the camera is moved (or alternatively the substrate is moved) so that the center of the lens of the camera is at different portions of the substrate. Images are acquired at these different portions of the substrate and subsequently clipped at the images outer regions where the image is distorted. In order to reconstruct the entire image of the substrate, the clipped images are stitched together to form one composite image of the entire substrate. For example, a substrate may be divided into 100 different sections, with 100 images taken where either the camera or the substrate moves so that the center of the lens is centered on each of the 100 different sections. Each of the 100 images is then clipped to save only the image of the specific section. Thereafter, the entire image is reconstructed by pasting each of the 100 images together to form one composite image of the entire substrate. This type of prior art system is very complex in operation and design. Motors to move either the camera or the substrate are required, increasing cost and complexity. Further, because either the substrate or the camera is moving, the system is prone to alignment problems. Finally, because a series of images are taken, acquiring one composite image may take several minutes.

Further, imaging systems require an imaging module in combination with a personal computer. The personal computer includes a standard desktop personal computer device with a processor, memory, monitor, etc. The imaging module includes the camera, substrate holder, controller and memory. The personal computer sends control instructions to the controller of the imaging module and receives the images for processing. Unfortunately, this distributed system is expensive due to the additional cost of the personal computer and large due to the separate space required by personal computer.

Moreover, once the image of the substrate is acquired, there are several difficulties in terms of identifying spots or the wells on the substrate. "Well" is a term used to identify a separate test or experiment on or within the substrate. Each well might contain a different sample or a different test of the same sample. With regard to the spots, prior art systems may have difficulty distinguishing between the background of the substrate and the spots on the substrate. With regard to identifying wells, prior art systems and methods require the operator to identify the regions of the slide in order to identify the well that the imaging system will analyze. However, this requirement of operator input to identify the wells on a slide is inefficient and prone to error.

Further, current systems and methods are unable to detect small concentrations of nanoparticle probes which are under 50 nm (and in particular gold nanoparticle probes). Therefore, the prior art has been forced to use probes which are greater than 50 nm. However, these greater than 50 nm probes are more difficult to use from a processing standpoint. Alternatively, prior art methods have attempted to amplify the nanoparticle probes under 50 nm, such as by using silver particles, in order to compensate for being unable to detect the smaller nanoparticles. However, these attempts to amplify the nanoparticles have proven unworkable. For example, in the case of silver amplification, it has proven difficult to use because it is reactive with light and temperature (creating storage and packaging issues), is fairly expensive and is very difficult to reproduce results accurately. The prior art has thus frequently rejected the use of silver amplification.

Accordingly, the prior art solutions do not solve the problem of detecting nanoparticles in a practical manner.

SUMMARY OF THE INVENTION

The present invention relates to the detection of metallic nanoparticles on a substrate. The substrate may have a plurality of spots containing specific binding complements to one or more target analytes. One of the spots on the substrate may be a test spot (containing a test sample) for metallic nanoparticles complexed thereto in the presence of one or more target analytes. Another one of the spots may contain a control spot or second test spot. Depending on the type of testing at issue, a control or a second test spot may be used. For example, when testing for infectious diseases, a control spot may be used (and preferentially control positive and control negative spots) to compare with the test spot in order to detect the presence or absence of a nucleic acid sequence in the test sample. This nucleic acid sequence could be representative of a specific bacteria or virus. The control positive spot may be a metallic nanoparticle conjugated directly to the substrate via a nucleic capture strand, metallic nanoparticles printed directly on the substrate, or a positive result of metallic nanoparticles complexed to a known analyte placed in a separate well. A second test spot may be used when testing for genetic disposition (e.g., which gene sequence is present). For example, two test spots are used for comparison of gene sequences, such as single nucleotide polymorphisms.

In one aspect, an apparatus for detection of metallic nanoparticles, with or without chemical signal amplification of the metallic nanoparticles, is provided. The apparatus comprises a substrate holder for holding the substrate, a processor and memory device, an imaging module, an illumination module, a power module, an input module, and an output module. In one embodiment, the apparatus may have a stationary substrate holder and imaging module. This allows for imaging of a substrate by the imaging module without the need for motors to move either the substrate, the imaging module or both. Further, the apparatus may have an imaging module which is proximate to the substrate holder. In order to reduce the size of the imaging apparatus, the imaging module (such as a photosensor) is placed near the substrate holder (which holds the substrate). For example, the imaging module may be in the range of 30 mm to 356 mm from the substrate. Due to this close placement, the acquired image is subject to distortion, particularly at the edges of the acquired image. In order to process the acquired image better, the apparatus compensates for this distortion. For example, the apparatus compensates for grayscale distortion using a grayscale distortion model. As another example, the apparatus compensates for spatial distortion using a spatial distortion model. In this manner, the effect of the distortion in the acquired image is lessened.

In another aspect of the invention, a method for automatically detecting at least some of the spots on the substrate is provided. An image is acquired of the plurality of spots composed of metallic nanoparticles, with or without signal amplification, on the surface of the substrate. In one embodiment, the metallic nanoparticles are subject to chemical signal amplification (such as silver amplification). Alternatively, the metallic nanoparticles are not subject to chemical signal amplification. Optionally, an optimal image is obtained based on an iterative process. The obtained image is corrected for distortion, such as grayscale distortion and spatial distortion. The grayscale distortion correction may be based on a model that compensates for brightness degradation of the image. The spatial distortion correction may be based on a model that compensates for spatial deformation of the image. Based on the compensated image, at least a portion of the spots on the substrate are detecting in the acquired compensated image. Optionally, thresholding (and preferably adaptive thresholding) may be performed in order to distinguish the spots in the image.

In still another aspect of the invention, a method for automatically detecting at least one of the wells on the substrate is provided. The method includes the steps of automatically detecting at least a portion of the spots on the substrate and automatically determining the wells based on the automatic detection of at least a portion of the spots. The detected spots are analyzed to determine, from the unordered collection of detected spots, how the spots are organized into wells. One manner of analysis is to detect the spatial differences between the spots. Based on the spatial differences, the spots may be organized into wells. Moreover, patterns of the characteristics of the spots (such as characteristics due to differences in spacing) may be analyzed to detect how the spots are organized into wells.

In yet another aspect of the invention, a method for detecting the presence or absence of the one or more of the target analytes in the test spot on a substrate is provided. The substrate has a plurality of spots containing specific binding complements to one or more target analytes. One of the spots is a test spot for metallic nanoparticles, with or without signal amplification, complexed thereto in the presence of one or more target analytes. Another spot is a control spot or a second test spot for metallic nanoparticles complexed thereto in the presence of a second or more target analytes. The method comprises the steps of acquiring multiple images of the test spot and the control or second test spot, the multiple images being taken at different exposures and determining presence of said metallic nanoparticle complexes in the test spot as an indication of the presence of one or more of the target analytes based on the acquired multiple images of the spots. The multiple exposures may be taken based on an "optimal" exposure time for a portion of the image (preferably optimal for one well on the substrate) and an exposure time which is less than the optimal exposure time.

Thus, an advantage of the present invention to provide an imaging system within a compact housing.

Another advantage of the present invention to avoid the necessity of using complex motorized systems to move the camera across the substrate.

Still another advantage of the present invention is the ability to detect spots and/or wells on the substrate without expensive or complicated implementations.

With the foregoing and other objects, advantages and features of the invention that will become hereinafter apparent, the nature of the invention may be more clearly understood by reference to the following detailed description of the invention, the appended claims and to the several views illustrated in the drawings.

DESCRIPTION OF THE FIGURES

FIGS. 16A-16D are examples of data which may be obtained by modifying the amount of light registering on the sample.

DETAILED DESCRIPTION OF THE PREFERRED EMBODIMENT(S)

Figure 1A:
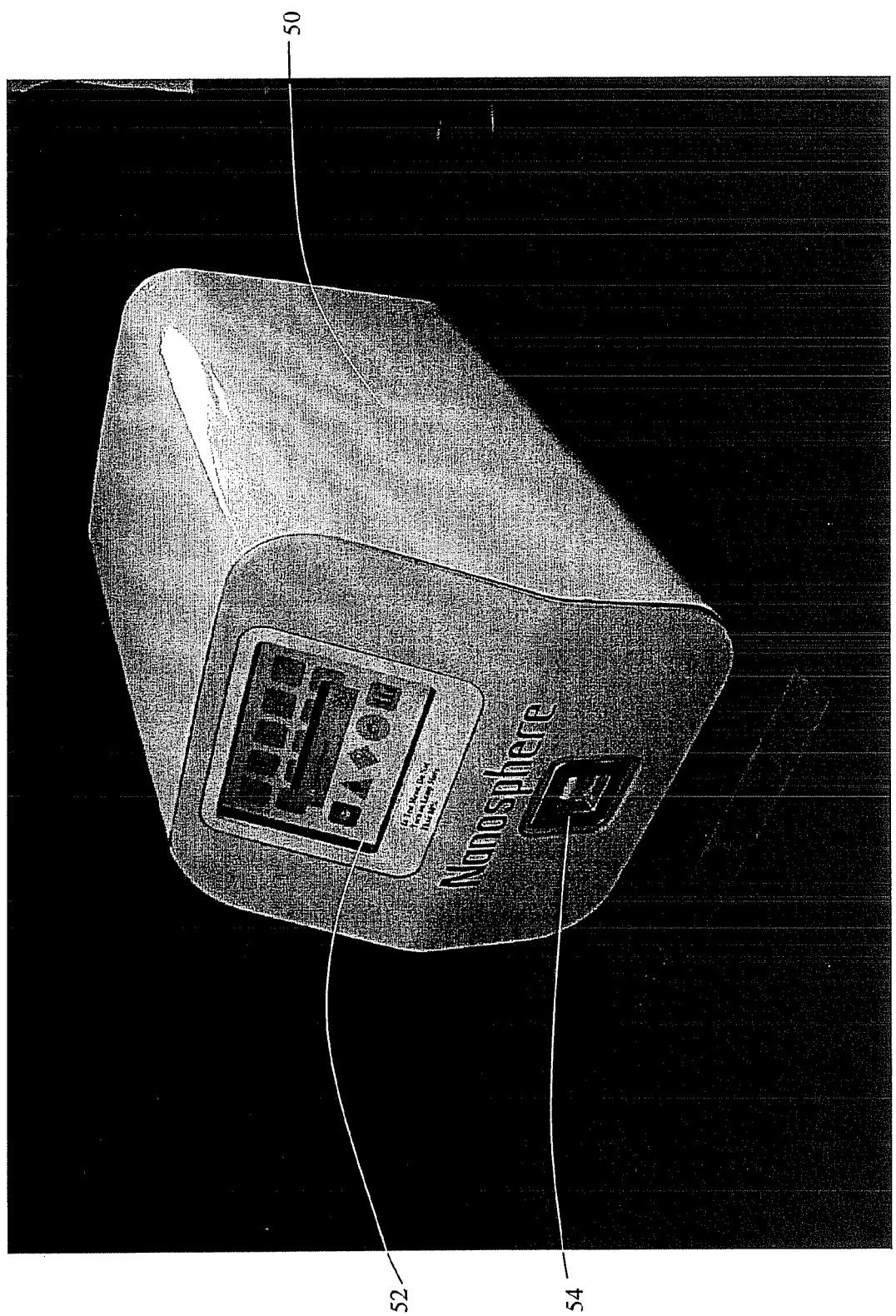
FIG. 1a is a perspective view of one embodiment of the imaging system.

The method and apparatus of the present invention relates to detection of metallic nanoparticles. In a preferred embodiment, the invention provides for methods and apparatuses for detection of gold colloid particles and for accurate reporting to the operator.

The examples set forth herein relate to an imaging system and method for detection of nanoparticles and in particular metallic nanoparticles. In a preferred embodiment, the nanoparticles are gold nanoparticles (either entirely composed of gold or at least a portion (such as the exterior shell) composed of gold) and amplified with silver or gold deposited post-hybridization on to the gold nanoparticles. The present invention may also be applied to other applications including, without limitation, detection of gold nanoparticles without silver or gold deposition.

As discussed in the background of the invention, there are several problems when detecting nanoparticles on a substrate including, for example: large sized systems occupying valuable space in a laboratory; complex motorized systems to move the camera across the substrate; problems in detecting spots and/or wells on the substrate that typically require expensive and complicated implementations. The present invention solves these and other problems of detecting nanoparticles in a manner that can be implemented for significantly less cost than current systems (less than US$10,000) and in an instrument footprint no larger than 18" by 12" by 12".

Definitions

"Analyte," or "Target Analyte" as used herein, is the substance to be detected in the test sample using the present invention. The analyte can be any substance for which there exists a naturally occurring specific binding member (e.g., an antibody, polypeptide, DNA, RNA, cell, virus, etc.) or for which a specific binding member can be prepared, and the analyte can bind to one or more specific binding members in an assay. "Analyte" also includes any antigenic substances, haptens, antibodies, and combinations thereof. The analyte can include a protein, a peptide, an amino acid, a carbohydrate, a hormone, a steroid, a vitamin, a drug including those administered for therapeutic purposes as well as those administered for illicit purposes, a bacterium, a virus, and metabolites of or antibodies to any of the above substances.

"Capture probe" as used herein, is a specific binding member, capable of binding the analyte, which is directly or indirectly attached to a substrate. One example of a capture probe include oligonucleotides having a sequence that is complementary to at least a portion of a target nucleic acid and may include a spacer (e.g, a polyA tail) and a functional group to attach the oligonucleotide to the support. Another example of a capture probe includes an antibody bound to the support either through covalent attachment or by adsorption onto the support surface. Examples of capture probes are described for instance, in PCT/US01/10071 (Nanosphere, Inc.) which is incorporated by reference in its entirety.

"Specific binding member," as used herein, is a member of a specific binding pair, i.e., two different molecules where one of the molecules, through chemical or physical means, specifically binds to the second molecule. In addition to antigen and antibody-specific binding pairs, other specific binding pairs include biotin and avidin, carbohydrates and lectins, complementary nucleotide sequences (including probe and captured nucleic acid sequences used in DNA hybridization assays to detect a target nucleic acid sequence), complementary peptide sequences, effector and receptor molecules, enzyme cofactors and enzymes, enzyme inhibitors and enzymes, cells, viruses and the like. Furthermore, specific binding pairs can include members that are analogs of the original specific binding member. For example a derivative or fragment of the analyte, i.e., an analyte-analog, can be used so long as it has at least one epitope in common with the analyte. Immunoreactive specific binding members include antigens, haptens, antibodies, and complexes thereof including those formed by recombinant DNA methods or peptide synthesis.

"Test sample," as used herein, means the sample containing the analyte to be detected and assayed using the present invention. The test sample can contain other components besides the analyte, can have the physical attributes of a liquid, or a solid, and can be of any size or volume, including for example, a moving stream of liquid. The test sample can contain any substances other than the analyte as long as the other substances do not interfere with the specific binding of the specific binding member or with the analyte. Examples of test samples include, but are not limited to: Serum, plasma, sputum, seminal fluid, urine, other body fluids, and environmental samples such as ground water or waste water, soil extracts, air and pesticide residues.

"Type of oligonucleotides" refers to a plurality of oligonucleotide molecules having the same sequence. A "type of" nanoparticles, conjugates, etc. having oligonucleotides attached thereto refers to a plurality of that item having the same type(s) of oligonucleotides attached to them.

"Nanoparticles having oligonucleotides attached thereto" are also sometimes referred to as "nanoparticle-oligonucleotide conjugates" or, in the case of the detection methods of the invention, "nanoparticle-oligonucleotide probes," "nanoparticle probes," "detection probes" or just "probes." The oligonucleotides bound to the nanoparticles may have recognition properties, e.g., may be complementary to a target nucleic acid, or may be used as a tether or spacer and may be further bound to a specific binding pair member, e.g., receptor, against a particular target analyte, e.g, ligand. For examples of nanoparticle-based detection probes having a broad range of specific binding pair members to a target analyte is described in PCT/US01/10071 (Nanosphere, Inc.) which is incorporated by reference in its entirety.

Substrates and Nanoparticles

The method and apparatus of the present invention may detect metal nanoparticles amplified with a silver or gold enhancement solution from any substrate which allows observation of the detectable change. Suitable substrates include transparent or opaque solid surfaces (e.g., glass, quartz, plastics and other polymers TLC silica plates, filter paper, glass fiber filters, cellulose nitrate membranes, nylon membranes), and conducting solid surfaces (e.g., indium-tin-oxide (ITO), silicon dioxide ($SiO_2$), silicon oxide (SiO), silicon nitride, etc.)). The substrate can be any shape or thickness, but generally will be flat and thin like a microscope slide or shaped into well chambers like a microtiter plate.

In practicing this invention, one or more different types of capture probes that bind to the target molecule are generally immobilized onto the surface of the substrate. The capture probe and the target molecule may be specific binding pairs such as antibody-antigen, receptor-ligand, and complementary nucleic acid molecules. See PCT/US)1/10071 (Nanosphere, Inc.) which is incorporated by reference in its entirety.

The presence of any target molecule-capture probe complex bound to the substrate is then detected using nanoparticle probes. Methods of making the nanoparticles and the oligonucleotides and of attaching the oligonucleotides to the nanoparticles are described in PCT/US01/10071 (Nanosphere, Inc.) and PCT/US01/01190 (Nanosphere, Inc.), which are incorporated by reference in its entirety. The hybridization conditions are well known in the art and can be readily optimized for the particular system employed.

The capture probes may be bound to the substrate by any conventional means including one or more linkages between the capture probe and the surface or by adsorption. In one embodiment, oligonucleotide as capture probes are attached to the substrate. The oligonucleotides can be attached to the substrates as described in, e.g., Chrisey et al., *Nucleic Acids Res.*, 24, 3031-3039 (1996); Chrisey et al., *Nucleic Acids Res.*, 24, 3040-3047 (1996); Mucic et al., *Chem. Commun.*, 555 (1996); Zimmermann and Cox, *Nucleic Acids Res.*, 22, 492 (1994); Bottomley et al., *J. Vac. Sci. Technol. A*, 10, 591 (1992); and Hegner et al., *FEBS Lett.*, 336, 452 (1993). A plurality of different types of capture probes may be arranged on the surface in discrete regions or spots in a form of an array which allows for the detection of multiple different target molecules or for different portions of the same target molecule.

The capture probes bound to the substrate surface specifically bind to its target molecule to form a complex. The target molecule may be a nucleic acid and the capture probe may be an oligonucleotide attached to the substrate having a sequence complementary to a first portion of the sequence of a nucleic acid to be detected. The nanoparticle-oligonucleotide conjugate has a sequence complementary to a second portion of the sequence of the nucleic acid. The nucleic acid is contacted with the substrate under conditions effective to allow hybridization of the oligonucleotides on the substrate with the nucleic acid or, alternatively, to allow hybridization of the nucleic acid with the nanoparticle-oligonucleotide conjugate. In yet another method the hybridization of the nucleic acid with the oligonucleotide on the substrate and the nucleic acid with the nanoparticle-oligonucleotide conjugate can be arranged to occur simultaneously. In one of these manners the nucleic acid becomes bound to the substrate. Any unbound nucleic acid and unbound nanoparticle-oligonucleotide conjugate is washed from the substrate before measuring the result of the DNA hybridization test.

The detectable change may be enhanced by silver staining. Silver staining can be employed with any type of nanoparticles that catalyze the reduction of silver. Preferred are nanoparticles made of noble metals (e.g., gold and silver). See Bassell, et al., *J. Cell Biol.*, 126, 863-876 (1994); Braun-Howland et al., *Biotechniques*, 13, 928-931 (1992). If the nanoparticles being employed for the detection of a nucleic acid do not catalyze the reduction of silver, then silver ions can be complexed to the nucleic acid to catalyze the reduction. See Braun et al., *Nature*, 391, 775 (1998). Also, silver stains are known which can react with the phosphate groups on nucleic acids.

Silver staining can be used to produce or enhance a detectable change in assays involving metallic nanoparticles performed on a substrate, including those described above. In particular, silver staining has been found to provide a huge increase in sensitivity for assays employing a single type of nanoparticle. For greater enhancement of the detectable change, one ore more layers of nanoparticles may be used, each layer treated with silver stain as described in PCT/US01/21846 (Northwestern University).

Figure 17:
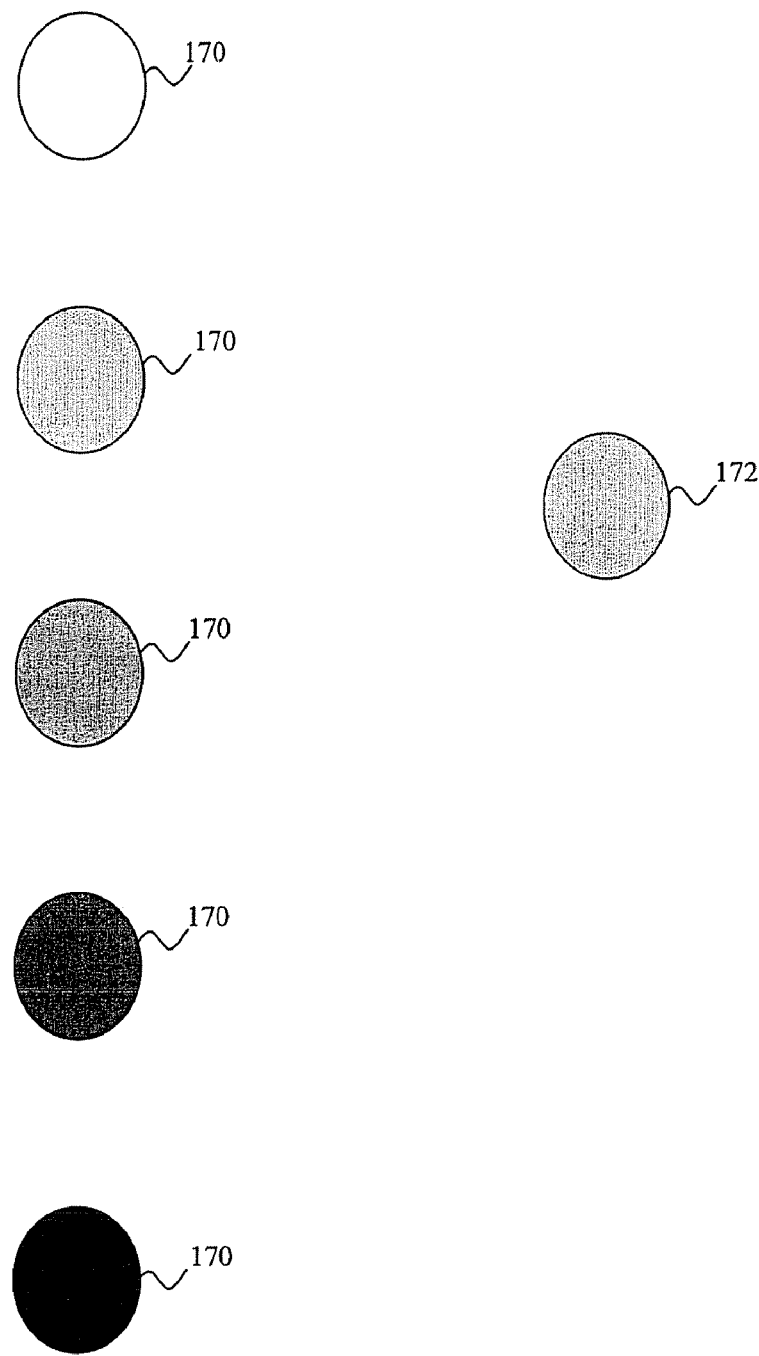
FIG. 17 is a representation of a series of control spots and a target test spot.

The oligonucleotides on the first type of nanoparticles may all have the same sequence or may have different sequences that hybridize with different portions of the nucleic acid to be detected. When oligonucleotides having different sequences are used, each nanoparticle may have all of the different oligonucleotides attached to it or, preferably, the different oligonucleotides are attached to different nanoparticles. FIG. 17 in PCT/US01/10071 (Nanosphere, Inc.) illustrates the use of nanoparticle-oligonucleotide conjugates designed to hybridize to multiple portions of a nucleic acid. Alternatively, the oligonucleotides on each of the first type of nanoparticles may have a plurality of different sequences, at least one of which must hybridize with a portion of the nucleic acid to be detected (see also FIG. 25B in PCT/US01/10071 (Nanosphere, Inc.)).

Alternatively, the first type of nanoparticle-oligonucleotide conjugates bound to the substrate is contacted with a second type of nanoparticles having oligonucleotides attached thereto. These oligonucleotides have a sequence complementary to at least a portion of the sequence(s) of the oligonucleotides attached to the first type of nanoparticles, and the contacting takes place under conditions effective to allow hybridization of the oligonucleotides on the first type of nanoparticles with those on the second type of nanoparticles. After the nanoparticles are bound, the substrate is preferably washed to remove any unbound nanoparticle-oligonucleotide conjugates. Silver stain treatment is then applied.

The combination of hybridizations followed by silver stain produces an enhanced detectable change. The detectable changes are the same as those described above, except that the multiple hybridizations result in a signal amplification of the detectable change. In particular, since each of the first type of nanoparticles has multiple oligonucleotides (having the same or different sequences) attached to it, each of the first type of nanoparticle-oligonucleotide conjugates can hybridize to a plurality of the second type of nanoparticle-oligonucleotide conjugates. Also, the first type of nanoparticle-oligonucleotide conjugates may be hybridized to more than one portion of the nucleic acid to be detected. The amplification provided by the multiple hybridizations may make the change detectable for the first time or may increase the magnitude of the detectable change. This amplification increases the sensitivity of the assay, allowing for detection of small amounts of nucleic acid.

If desired, additional layers of nanoparticles can be built up by successive additions of the first and second types of nanoparticle-oligonucleotide conjugates. In this way, the number of nanoparticles immobilized per molecule of target nucleic acid can be further increased with a corresponding increase in intensity of the signal.

Also, instead of using first and second types of nanoparticle-oligonucleotide conjugates designed to hybridize to each other directly, nanoparticles bearing oligonucleotides that would serve to bind the nanoparticles together as a consequence of hybridization with binding oligonucleotides could be used.

The Imaging System

The presently preferred embodiments of the invention will now be described by reference to the accompanying figures, wherein like elements are referred to by like numerals. Referring to FIG. 1a, there is shown a perspective view of one embodiment of the imaging system. The imaging system 50 includes a display 52 and a handle 54 for accessing a tray that holds the substrate during imaging. The entire imaging system is approximately 12" in width, 12" in height and 18" in depth (as shown by the 12" ruler which is placed proximate to the display of the imaging system 50 in FIG. 1a). As discussed in the background of the invention, prior art systems were large in size, occupying a significant portion of space in the laboratory. By contrast, the present imaging system is compact due to several factors. Examples of those factors, discussed in more detail below, include: a sensor (such as a photosensor) being placed close or proximate to the substrate/ substrate holder; software to compensate for distortion in the image acquired by the sensor; and processor/memory and all control functions resident within the imaging system 50.

Figure 1B:
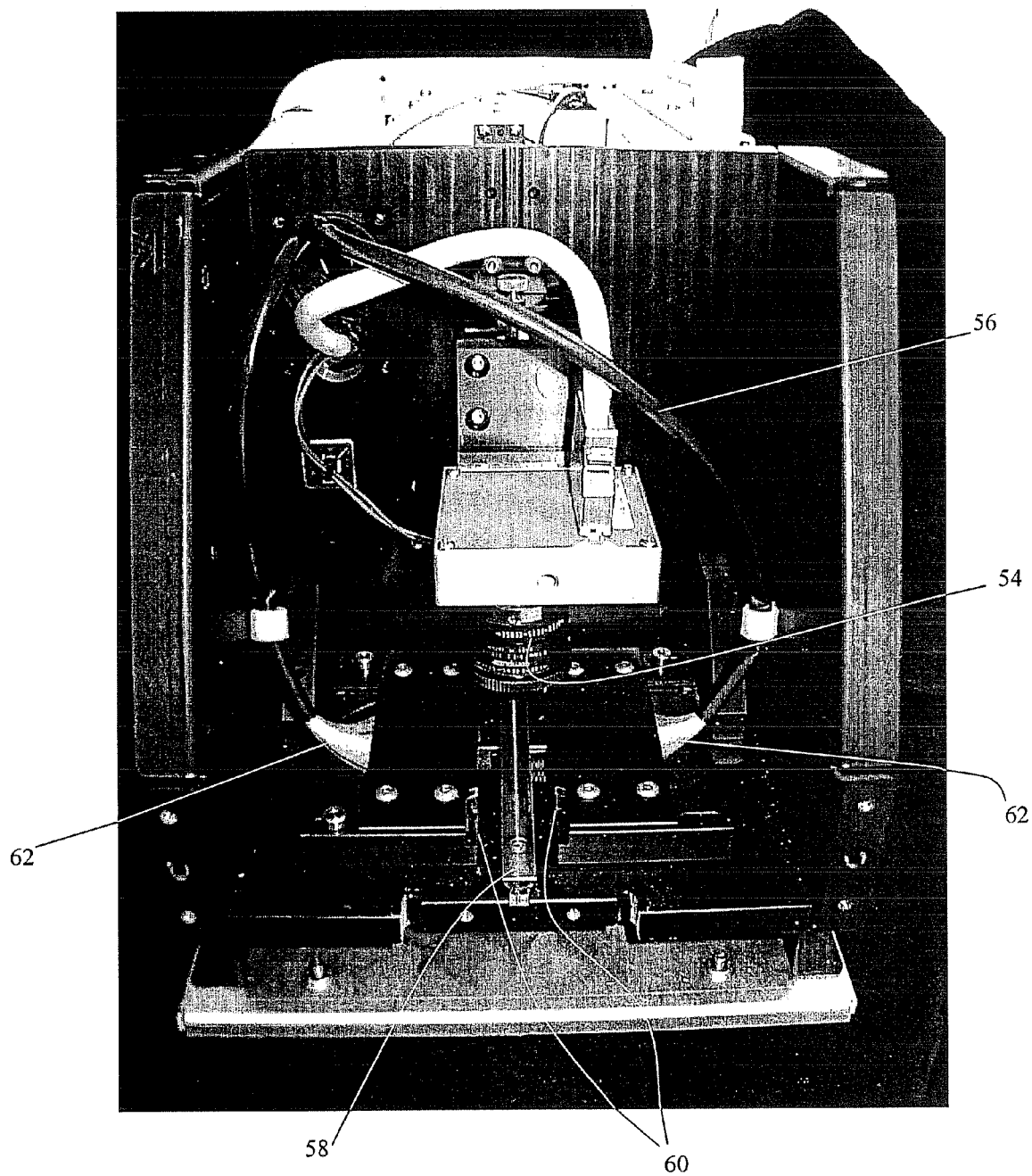
FIG. 1b is a front view of the imaging system shown in FIG. 1a with the front cover removed.

Referring to FIG. 1b, there is shown a front view of the imaging system shown in FIG. 1a with the front cover removed. The substrate is placed in a substrate holder with a base 58 at least one sidewall 60 (and preferably two sidewalls). Typically, the substrate may have dimensions of a standard microscope slide (25 mm by 75 mm). Larger or smaller substrates may be used. The substrate is illuminated by an illumination module, as discussed in detail with respect to FIG. 2. One type of illumination module uses fiber optic lines to sidelight the substrate. As shown in FIG. 1b, a plurality of fiber optic lines 62 feed into at least one of the sidewalls 60 (and preferably both of the sidewalls, as shown in FIG. 1b). Therefore, when the substrate is placed on base 58 in between sidewalls 60, light is sent via the fiber optic lines 62 to the side of the substrate. The substrate is illuminated so that nanoparticles on the substrate scatter light which is captured by a sensor, as discussed in detail with respect to FIG. 2.

One type of sensor is a photosensor (not shown in FIG. 1b) and at least one lens 54. The photosensor, in a preferred embodiment, is stationary. Further, the photosensor may be a CMOS photosensor by Silicon Video Model Number 2112. The dimensions of the CMOS photosensor by Silicon Video Model Number 2112 is a rectangle with a diagonal of 12.3 mm (1288 pixels by 1032 pixels). The lens 54 is an 8.5 mm focal length lens. The photosensor sends imaging data via a cable 56 to a processor, as discussed subsequently. As shown in FIG. 1b, the lens 54 is proximate to the substrate/substrate holder. In one embodiment, the sensor/lens is placed at 356 mm distance from the substrate/substrate holder. In a preferred embodiment, the housing of the photosensor is placed approximately 68 mm from the substrate/substrate holder. The working distance, which is the distance between the object and image, is a function of the substrate dimensions. It is expected that varying substrate dimensions will be used depending on different business applications such as pharmacogenomics, clinical research, agribusiness genomics, etc. The preferred embodiment will be such that working distance can be easily modified in the factory between 30 mm and 356 mm to obtain various fields of view. The use of lens spacers allows this large range in working distances. Further, as shown in FIG. 1b, the sensor and the lenses are stationary with respect to the substrate being imaged. Because of the close distance between the sensor and the substrate and because the sensor/substrate are stationary, a large amount of distortion occurs, particularly at the edges of the field of view. As discussed subsequently, the image acquired by the sensor is modified to compensate for the distortion. This is in contrast to certain prior art devices, discussed in the background section, which move either the camera or the substrate or both to compensate for distortion. In one embodiment, the imaging system 50 may further comprise a conveyor system, such as a carousel based system, whereby substrates may be rotated or translated in and out of the field of view to allow batching of multiple substrates for a high-throughput implementation of the device. For example, a plurality of substrates may be placed on a carousel. The carousel may be rotated via a motor (such as a stepper motor) so that a substrate may be moved into and out of the field of view of the sensor. The substrate however need not be moved during imaging.

Figure 1C:
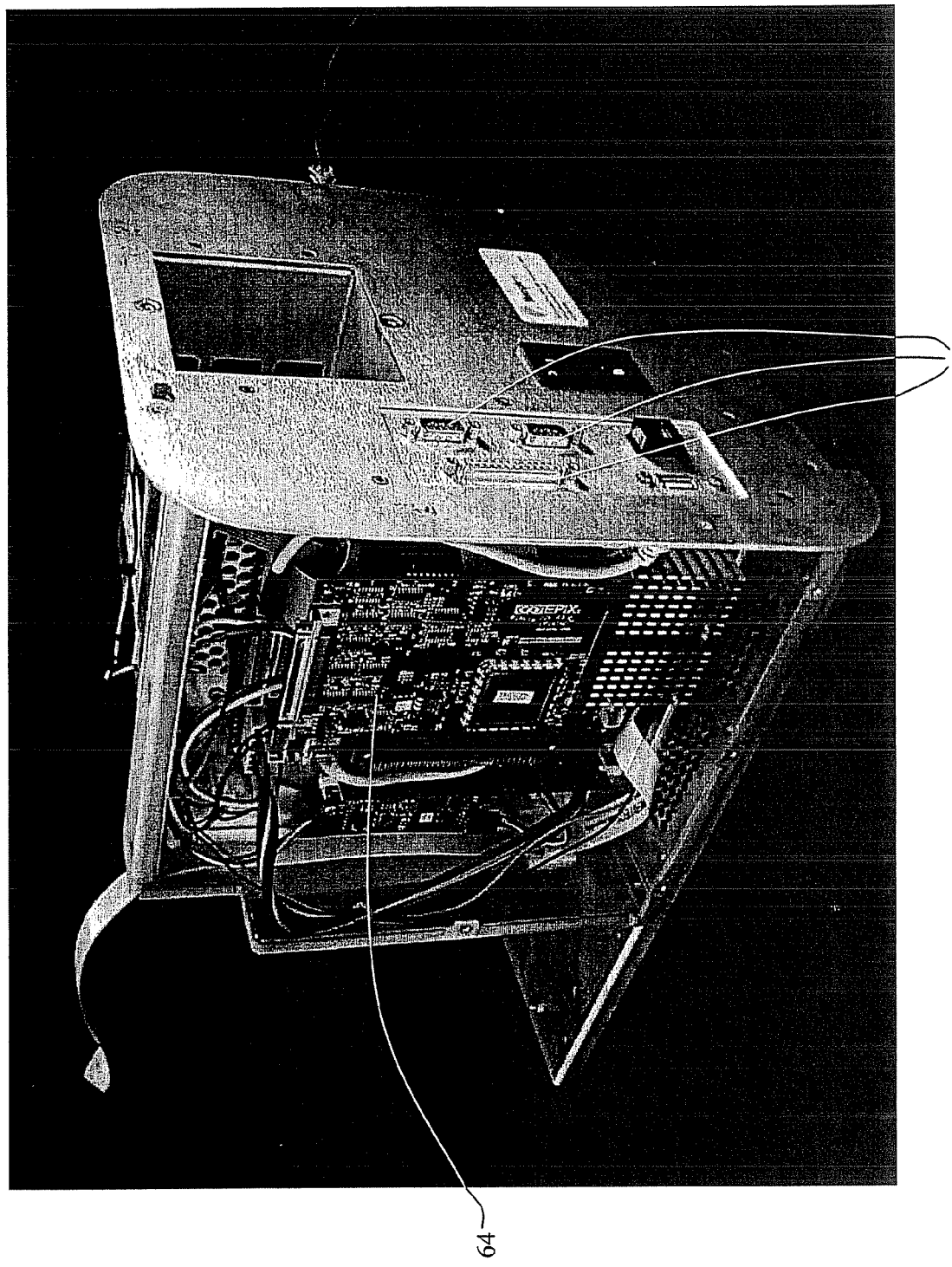
FIG. 1c is a side perspective view of the imaging system shown in FIG. 1a with the front cover removed.

Referring to FIG. 1c, there is shown a side perspective view of the imaging system shown in FIG. 1a with the cover removed. In one embodiment, the imaging system includes a microprocessor and memory resident within the housing of the imaging module, as discussed in detail with respect to FIG. 2. As shown in FIG. 1c, there are various circuit boards 64 within the imaging system including a single board computer (which contains the microprocessor, memory and some electronic I/O), a photosensor capture board (which captures images from the sensor and buffers the images for the processor to access), a custom input/output board (which receives sensor data, controls the user input/output and some electronic input/output).

Figure 2:
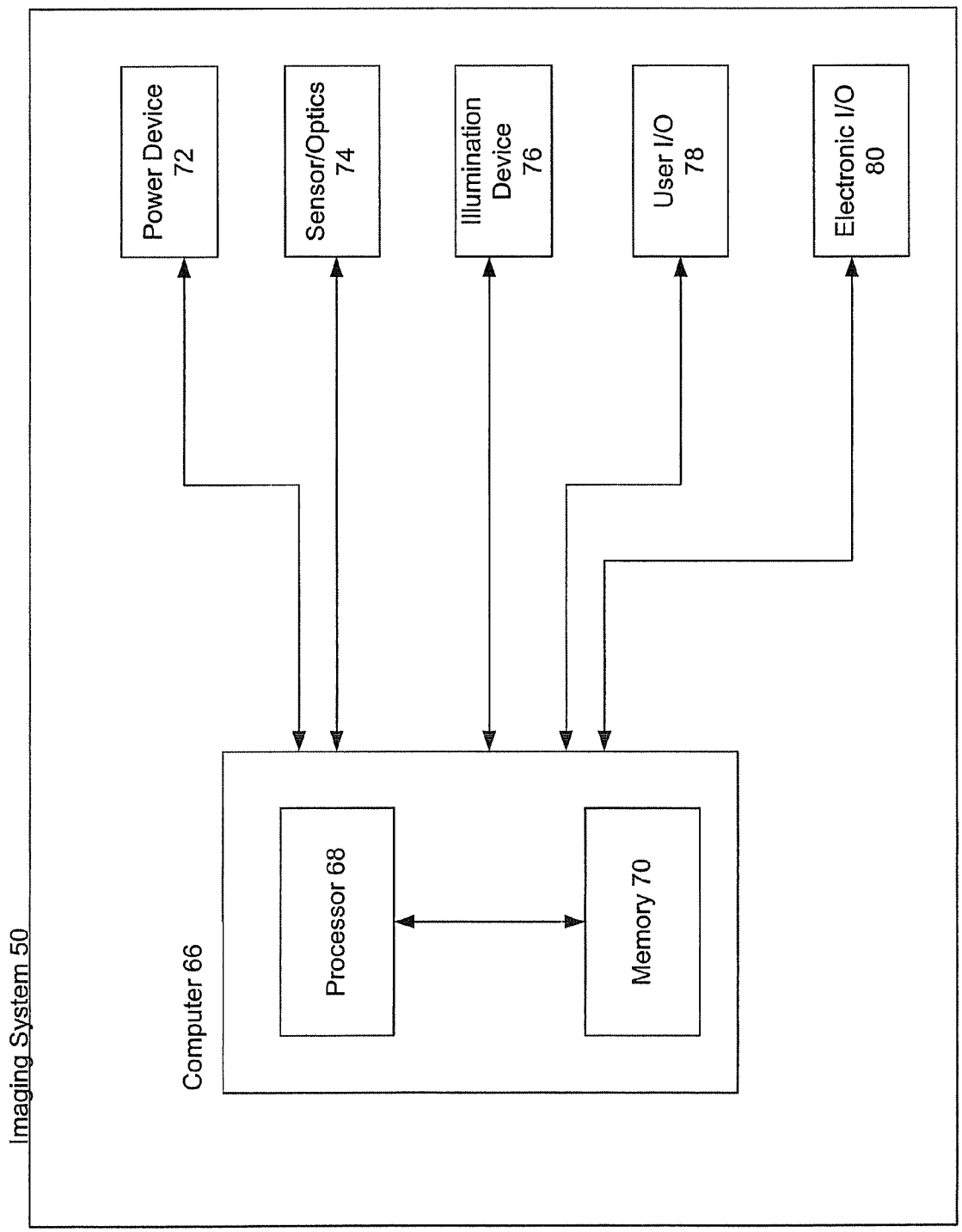
FIG. 2 is a block diagram of the system in FIGS. 1a-c.

Referring to FIG. 2, there is shown a block diagram of the system in FIGS. 1a-c. The imaging system 50 includes a computer 66. The computer includes a processor and a memory device located on a printed circuit board (as shown in FIG. 1c) within the housing of imaging module 50. Prior art systems use an imaging module which interfaces with a standalone desktop computer. This type of distributed system is expensive due to the additional cost of a complete personal computer designed for many functions and is inefficient due to separate space required by the personal computer. By contrast, one aspect of the present invention embeds the processor 68/memory 70 functionality within the imaging module and is designed to be dedicated to its specific function which can significantly reduce cost and complexity. The processor 68 may comprise a microprocessor, a microcontroller, or any device which performs arithmetic, logic or control operations. The memory 70 may include non-volatile memory devices such as a ROM and/or volatile memory devices such as a RAM. The memory 70 may store program(s) for spot detection/well identification and/or image analysis, which are discussed subsequently as well as the results of numerous DNA hybridization tests. The processor 68 may access the memory 70 in order to execute the program(s). In this manner, the imaging module shown in FIGS. 1a-c is a standalone and compact device.

The imaging system also includes an illumination module 76. The illumination module 76 illuminates the sample with electromagnetic radiation. In one embodiment, the illumination module illuminates the sample with electromagnetic radiation in the visible light spectrum. Alternatively, light from other wavelengths such as infrared and ultraviolet may be used. Further, the illumination module may generate a specific wavelength of light, due to laser generation, or a spectrum of wavelengths, such as white light.

A variety of illumination modules may be used, such as side-lighting, front-lighting, and backlighting. Polarizers and filters can also be used to modify the incident light. When side-lighting, the illumination module may couple light to at least one side of the substrate so as to utilize the waveguiding capabilities of glass or another suitable substrate. Coupling of the illumination module to the support media may be accomplished in a variety of ways such as by a fiber optic bundle, a solid waveguide, a laser beam or LEDs glancing along the substrate. FIG. 1b shows an example of side-lighting by using fiber optic lines to couple light to the sides of the substrate. As another example, the illumination module may employ front-lighting. When front-lighting, the sensor is typically positioned directly above the substrate and the illumination module is placed at a position such that the specular reflection misses the photosensor, but that the photosensor detects light scattered from the metallic nanoparticles. Depending on the application of the system, the illumination module may be placed at a variety of angles relative to the surface of the substrate. As still another example, the illumination module may employ backlighting. The sensor may be placed directly above the substrate (as when front-lighting) and the illumination module may be placed behind the substrate (and preferably directly behind the substrate). Since the nanoparticles should not transmit light (i.e., backscatter the light) through them, the portions of the substrate which contain nanoparticles will appear as dark or darker spots relative to other sections on the substrate. In still another example, the illumination module may employ polarizers. Two polarizers positioned nearly at 90° of one another may be used in combination with either front- or backlighting to detect the change in refractive index of light scattered by the metallic nanoparticles which also causes a change in the angle of polarization. In this embodiment the light transmitted through the substrate or specularly reflected by the substrate is filtered by the polarizers but light scattered by the metallic nanoparticles is readily detectable. An embodiment that uses diffuse axial illumination has shown applicability with and without polarizers. In this method, light is directed perfectly normal to the substrate and the resultant reflected light from the spots of nanoparticles is detected. Polarizers or opaque substrate materials with anti-reflective coatings as necessary can be used to dampen the specular reflection from the substrate.

The imaging module further includes at least one photosensor 74. A photosensor frequently used is a CCD or CMOS based sensor. The photosensor senses electromagnetic radiation, converts the sensed electromagnetic radiation into a data format and sends the data to processor 68. In a preferred embodiment, the sensor senses light in the visible light spectrum. Alternatively, the sensor may sense light in other bands of the electromagnetic spectrum, such as the infrared and ultraviolet bands. The photosensor, is composed of a plurality of pixels (e.g., 1.2 million pixels) although other size formats can be used. The amount of visible light which impinges on each pixel is converted into a data format. One such data format is a numerical value assigned to the amount of light which has impinged on the pixel. For example, if the data output of a pixel has a range of numerical values from 0 to 1023 ($2^{10}$ bits of data per pixel), 0 represents no light which has impinged on the pixel and 1023 represents saturation of the pixel. In this manner, if light impinges on the pixel after saturation, there is no change in the numerical value assigned. For example, the numerical value will remain at 1023 even if additional light impinges on the pixel after saturation. As discussed subsequently, the processor 68 may control the operation of the sensor (such as by controlling the exposure time) in order to modify the amount of light registered by the sensor.

Moreover, a lens or a series of lenses may be connected or coupled to the sensor to capture more of the scattered or reflected lightwave. In a preferred embodiment, the sensor works in conjunction with a single stationary lens, as shown in FIG. 1b. Alternatively, multiple lenses and mirrors can be used to refract and reflect the incident light on to the image as well as the light scattered or reflected from the nanoparticle spots.

The imaging system 50 may also include user input/output (I/O) 78. The user I/O 78 includes a display and a touch screen module as well as input scanners like a bar code wand. Alternatively or in addition, the user I/O may include a keyboard. The imaging module 50 further includes electronic I/O 80. The electronic I/O 80 may include data ports 55 which may interface with a network, such as a LAN, or may interface with an electronic device, such as a printer. The imaging system includes a power module, as shown at block 72. The power module 72 powers the various modules in the imaging system including the computer, the photosensor 74, the illumination module 76, the user I/O 78 and the electronic I/O 80.

Figure 3:
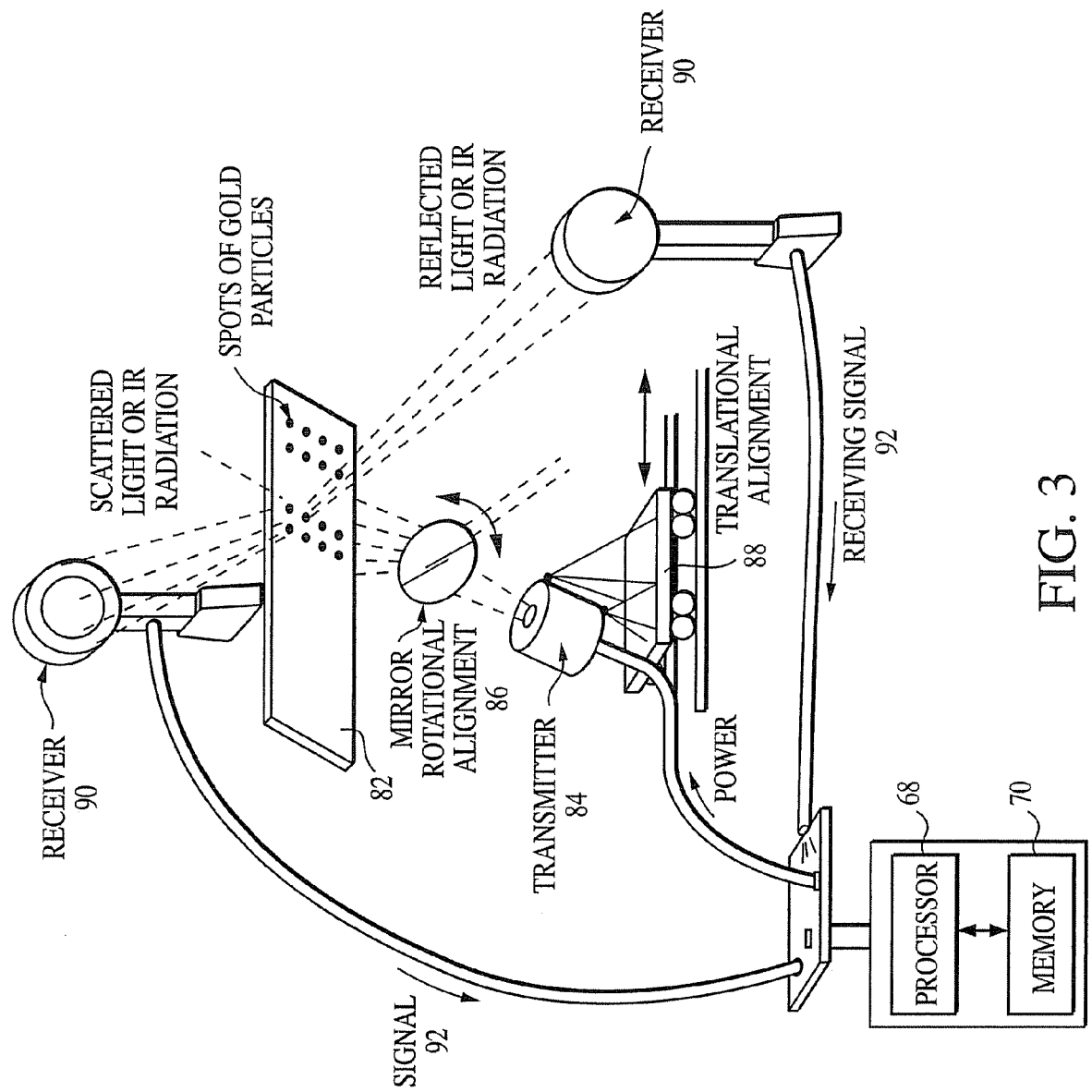
FIG. 3 is another diagram of the imaging system according to alternated embodiment of the system.

Referring to FIG. 3, there is shown another diagram of the imaging system according to another embodiment of the system. Similar to FIG. 1b, samples are placed on a substrate 82. The substrate 82 is illuminated using a transmitter 84. The transmitter 84 is controlled by processor 68, which sends power and commands regarding the placement of the beam (in one embodiment, the processor 68 controls the transmitter by sending commands regarding the translational alignment of the transmitter 84 and/or the rotational alignment of the mirror 86 of the transmitter 84). The beam may then be sent to the substrate 82, whereupon light or IR radiation is scattered upon encountering of spots of gold particles. The beam from the transmitter may be directed to any portion of the substrate 82. In one embodiment, the beam is rotationally aligned using a mirror 86 and translationally aligned using a movable platform 88. Any means may be used to move the transmitter 84 in any one of three dimensions. Alternatively, rather than moving the transmitter 84, the substrate 82 may be moved in any one of three dimensions. The scattered light may then be sensed by at least one sensor. As shown in FIG. 3, the sensors take the form of receivers 90 which are placed on either side of the slide. More or fewer receivers may be used. The signals 92 from the receivers 90 may then be sent to the processor 68 for analysis, as discussed subsequently.

Figure 4:
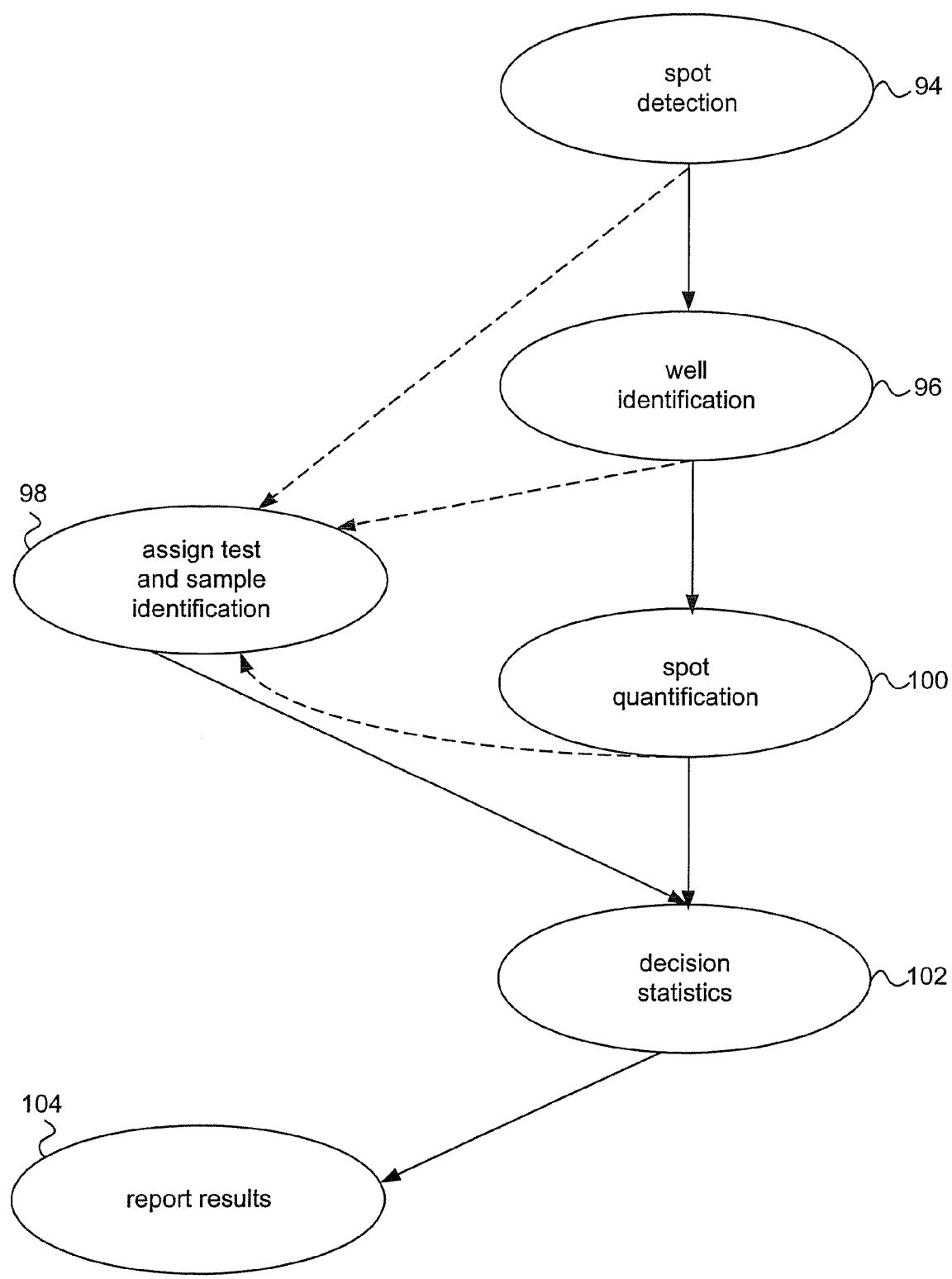
FIG. 4 is a flow chart for the imaging system of FIGS. 1a-c.

The imaging system of FIGS. 1a-c automatically detects the spots/wells on the substrate, automatically quantifies the spots on the substrate, and automatically interprets the spots based on decision statistics. Referring to FIG. 4, there is shown a flow chart for the imaging system of FIGS. 1a-c. After the substrate is placed in imaging system 50, at least some of the spots on the substrate are detected, as shown at block 94. This step of spot detection is discussed in more detail in the flow chart of FIG. 5. Based on some or all the spots detected, some or all of the wells are identified, as shown at block 96. This step of well identification is discussed in more detail in the flow chart of FIG. 6. Test and sample identification are assigned to the various spots/wells, as shown at block 98. Test identification may indicate whether a particular spot is a target or a control spot and if a target spot then the function of the test is identified. Sample identification may indicate the origin of the spot (e.g., a specific patient identification). These test and sample identification data may be input either manually, such as by an operator, or automatically, such as by using a legend on the substrate. The legend may comprise using a code (e.g. bar code) on the substrate. As discussed previously, the user I/O 78 may include a bar code reader wand. The bar code reader may be resident within or adjacent to imaging system 50. The bar code reader may read a bar code which is placed on a substrate. Alternatively, or in addition to, a code to identify test and/or sample identification may be placed on the slide for processing. As discussed in further detail below, the substrate may be composed of a plurality of spots. A sequence of spots (preferably in a line) may represent data to indicate test and/or sample identification data. For example, the data in the sequence of spots may be in a binary format (presence of nanoparticles=1, absence of nanoparticles=0) to represent a particular number.

Further, the step of assigning the test and sample identification may be performed prior to or in parallel with the steps of spot detection, well identification and/or spot quantification. Alternatively, the step of assigning the test and sample identification may be performed after the steps of spot detection, well identification and/or spot quantification. As shown at block 100, the spots are quantified. This step of spot quantification is discussed in more detail in the flow chart of FIG. 7. As shown at block 102, the step of decision statistics is performed. The outputs of the steps of spot quantification and assigning test and sample identification are analyzed to interpret the results based on a statistical analysis. This step of decision statistics is discussed in more detail in the flow chart of FIG. 8. The results of the decision statistics are reported, as shown at block 104. The results may be output using the User I/O, as shown at block 78 of FIG. 2.

As discussed above, one aspect of the invention is the automatic detection of the spots/wells on the support media. In a preferred embodiment, the software automatically detects the location of the wells in the image and identifies the locations of the specific areas in the well where spots of DNA have been deposited and hybridized. One method to the detection of wells is to use a series of image processing techniques to first extract some or all of the probable spots within the image. Then, analysis, such as geometric analysis, of the spot locations attempts to determine the location of the wells.

Spot Detection

Detection of one, some or all of the spots on a substrate is difficult to perform. The surface area of the spots can be a very small portion of the entire image contributing to the difficulty of detecting the spots. For example, in the context of an image being composed of pixels, the spot may be on the order of 100 pixels or less within an entire pixel area of 1.2 million pixels. In addition, dirt, dust or the like may cause noise in the acquired image. Optionally, an "optimal" image of at least some (and preferably all) of the hybridized spots on the substrate is acquired. This "optimal" image may optionally be modified to correct for distortions in the image. After which, thresholding may be used to analyze the image to determine background (e.g., black portion of image) versus foreground objects (e.g., white portion of image). As one example of this background/foreground analysis, adaptive thresholding calculates the foreground/background separation based on a local neighborhood of image data values. The result typically is a collection of white areas against a black background. However, it can also be a foreground of dark spots against a relatively white background. The foreground areas of the image, derived by threshold analysis, may then be analyzed to determine whether these areas conform to a predetermined spot area. For example, characteristics of the foreground areas, such as area, mass, shape, circumference, etc. of the foreground areas, may be compared with predetermined characteristics of the spots, such as area, mass, shape, circumference, etc. If the characteristics of the foreground area(s) are comparable to the characteristics of the spots, the foreground area(s) is/are deemed a spot for purposes of well detection.

Figure 14:
FIG. 14 is an example of an image of the spot detection method where it has detected the bright spots in the image.

In the context of a sensor which measures light based on pixels, a pixel image and preferably an "optimal" pixel image) is subjected to threshold analysis to separate foreground pixels from background pixels. After which, the image may be scanned to identify pixel clusters that define objects. These objects may then be arranged into "blobs" with these blobs being analyzed to determine their characteristics, such as area, mass, shape, circumference, etc. The characteristics of the blobs are then compared with the expected characteristics of the DNA spots to filter out noise. Referring to FIG. 14, there is shown an example of an image of which the described spot detection method was used to identify typical DNA hybridization spots.

Figure 5:
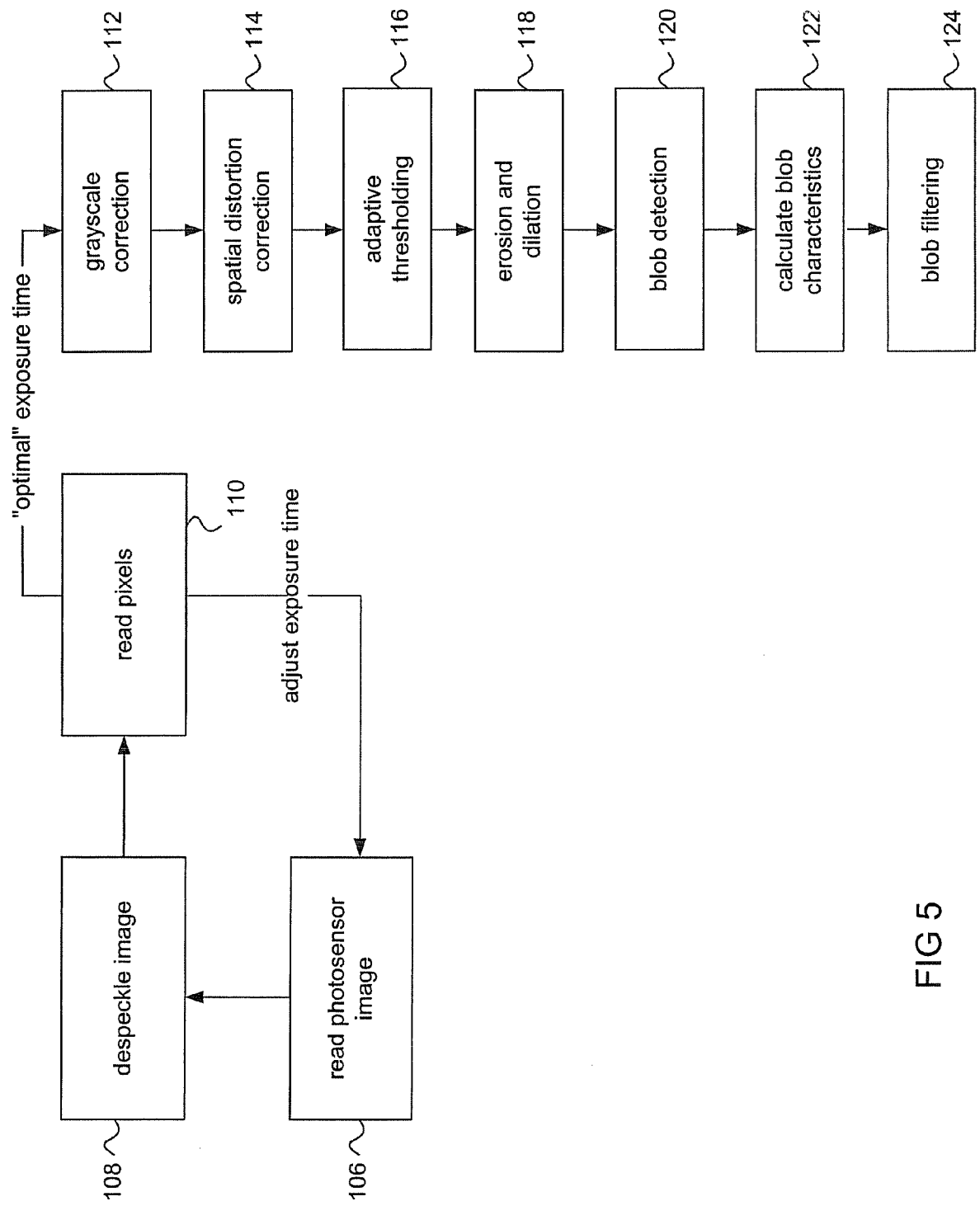
FIG. 5 is a flow chart of one embodiment of spot detection on the substrate, as discussed in FIG. 4.

Referring to FIG. 5, there is shown a flow chart of one embodiment of spot detection on the substrate, as discussed in FIG. 4. In one aspect of the present invention, an image of at least a portion of the substrate is acquired. In a preferred embodiment, the image acquired includes all of the spots on the substrate. Alternatively, the image acquired may include only a portion of the spots on the substrate (e.g., such as by obtaining the image of all the spots and processing only a portion of the image). Prior to analyzing an image for spot detection, one may iterate to determine an "optimal" image. "Optimal" may be defined as the amount of electromagnetic radiation registered by the sensor which, based on the sensor's characteristics, may best enable the detection of spots on the substrate. For example, the "optimal" image may be defined as a percentage of saturation of the sensor. As discussed above, a sensor may saturate when additional light impinging on the sensor (or a portion of the sensor) yields no additional data. In the context of a photosensor which uses pixels, saturation occurs when the pixel value is at its maximum. Different percentages of saturation may be chosen as the optimal image, such as 0.5%, 1%, 5%, 10% etc. Another definition of an "optimal" image is an image that returned the maximum number of identified spots. In this definition, the sensor's read time, or exposure time, may be adjusted until the maximum number of spots are detected.

There are several ways, discussed in more detail below, of modifying the amount of light registered to the sensor. In one aspect, the amount of light registered by the sensor may be controlled by the modifying parameters that control the operation of the sensor. Examples of parameters for the sensor include, but are not limited to, exposure time and sensor gain. In the case of exposure time, the amount of time for exposure of the sensor to the impinging light directly affects the amount of light registered by the sensor. Reducing/increasing the exposure time reduces/increases the amount of light. Where the sensor is a photosensor, the exposure time is modified by adjusting the time at which the pixels of the photosensor are read. Typically, for a digital sensor the exposure time controls an integration time. The sensor element values, the pixels, are read at the conclusion of the integration time. For example, if an exposure time of 60 mSec is desired, the photosensor is initialized and the pixel values are read 60 mSec after initialization. In another aspect, the amount of light registered by the sensor may be controlled by modifying parameters controlling the illumination module. Similar to the sensor, each illumination module has parameters controlling its operation. Examples of parameters for the illumination module include, but are not limited to, amount of time the illumination module is turned on, intensity of illumination module, etc.

Referring to blocks 106, 108 and 110, the flow chart iterates until an "optimal" image is obtained. An initial value of the exposure time for the sensor is chosen. Based on this initial exposure time, the photosensor reads the image, as shown at block 106. Because of noise in the system due to dirt, dust, etc., the image may optionally be despeckled, as shown at block 108. The despeckling may be achieved by applying a filter, such as a configurable median filter or mean filter in order to despeckle the image and remove any sharp signal spikes. A median filter considers each pixel in the image in turn and looks at its nearby neighbors to decide whether or not it is representative of its surroundings. The median filter replaces the pixel value with the median of neighboring pixel values. By contrast, the mean filter replaces the pixel value with the mean of neighboring pixel values. The median is calculated by first sorting all the pixel values from the surrounding neighborhood into numerical order and then replacing the pixel being considered with the middle pixel value. (If the neighborhood under consideration contains an even number of pixels, the average of the two middle pixel values is used.)

After the image is despeckled, the pixels are read, as shown at block 110. Based on the read pixels, the processor 68 analyzes the pixels to determine whether the image is "optimal." If the definition of "optimal" is based on the percentage of saturation of the pixels within the image, the processor 68 sums the amount of saturation within the image (e.g., determining the number of pixels within the image which are at saturation). If the percentage calculation is less than the "optimal" amount (i.e., less pixels are saturated than "optimal"), the exposure time is increased. Alternatively, if the percentage calculation is greater than the "optimal" amount (i.e., more pixels are saturated than "optimal"), the exposure time is reduced. The process iterates by changing the exposure time until the optimal image is obtained.

Once the optimal image is obtained, it is analyzed to determine the location of one, some or all of the spots on the substrate. To achieve an imaging system within a very small footprint for an instrument, the imaging system operates on a short optical working distance (i.e., the sensor is so close to the substrate). However, this short optical working distance results in an acquired image that is subject to distortion, particularly at the edges of the field of view. As discussed in the background of the invention, it is undesirable to limit the field of view since it would result in an undesirable requirement to move the camera across the object image, clipping and stitching, a series of images. Preferably and optionally, compensation of the acquired image is performed. Examples of distortion include, but are not limited to grayscale distortion and spatial distortion.

Distortion occurs when an optical system is forced to use a working distance that is shorter than desired for a given sensor size and field of view. This implementation is forced when marketing requirements force a low cost system, which mandates the use of off-the-shelf, high volume parts coupled with another market requirements, which is a small instrument footprint. In a preferred implementation, the low-cost, high-volume photosensor with a 9.7 mm horizontal is being forced to image a 65 mm horizontal field of view with a working distance somewhere between 30 mm and 356 mm. The resulting distortion grows as the working distance is reduced.

Figure 9A:
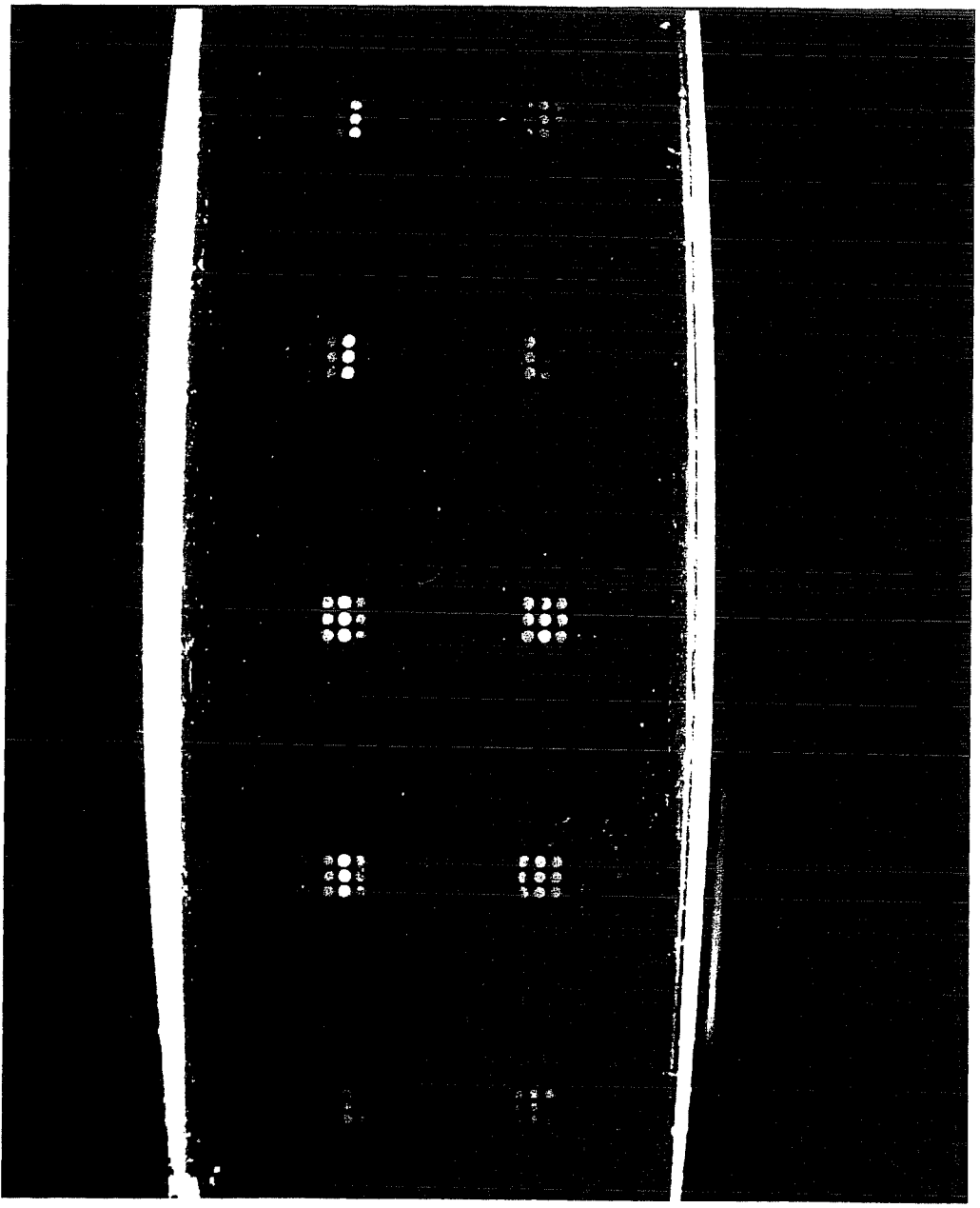
FIGS. 9a and 9b are images of a slide before and after grayscale correction.
Figure 9B:
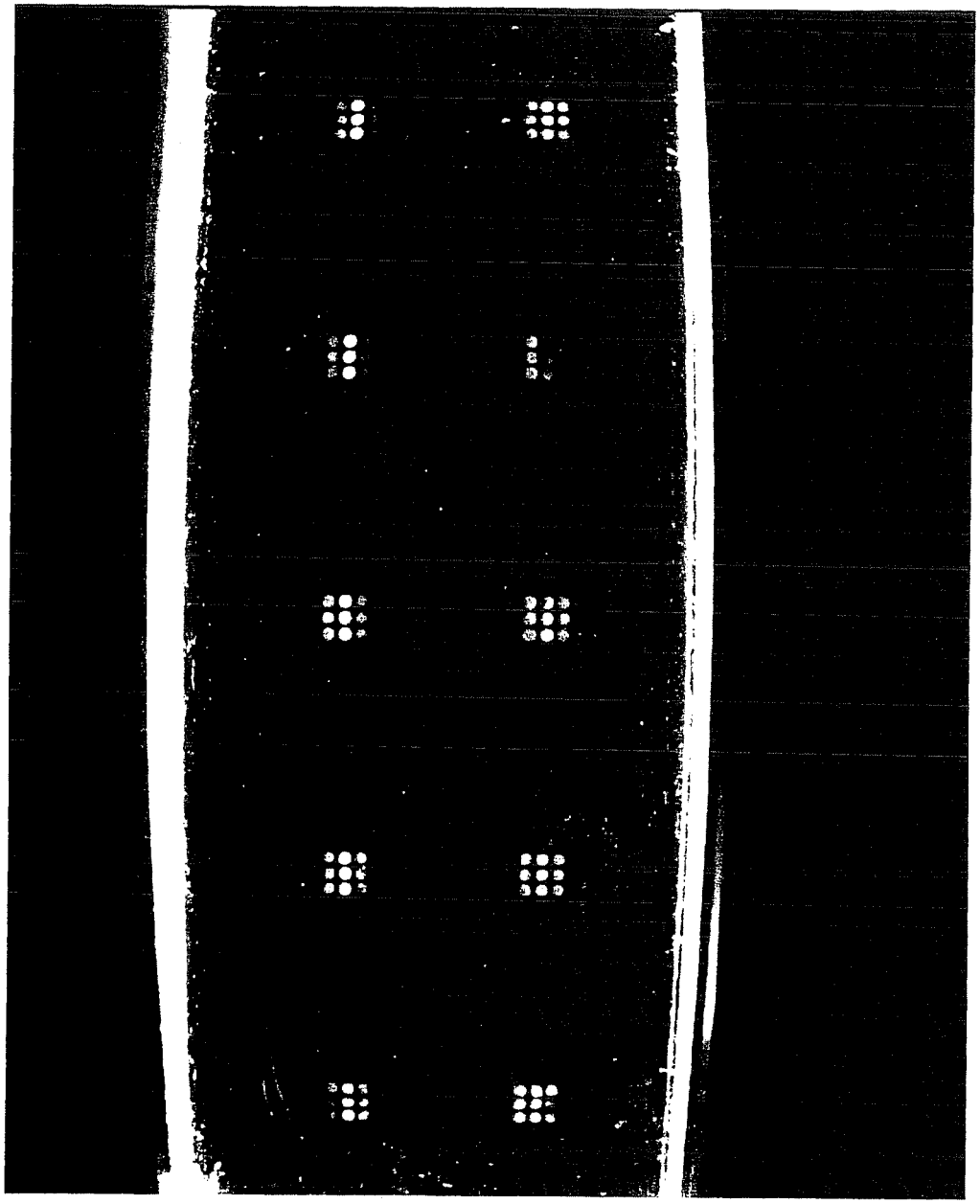
Figure 10:
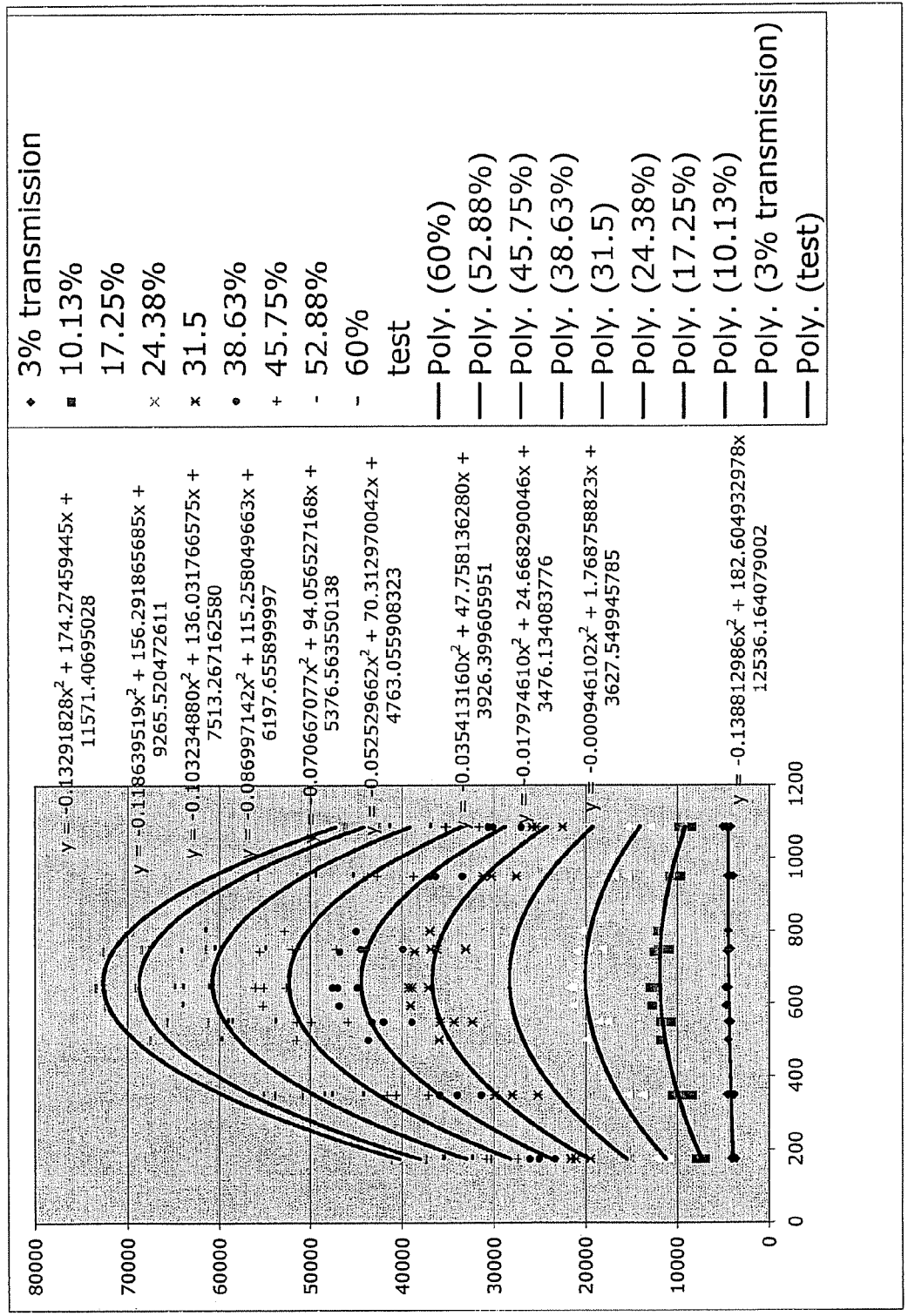
FIG. 10 is a graph of the compensation model in one dimension for brightness across the field of view in order to correct grayscale distortion.

The distortion in the preferred embodiment manifests itself in both spatial deformation of the image and brightness degradation of the image. The distortion, both spatially and brightness, increases as a function of the distance from the center of the lens. An example of grayscale distortion is shown in FIG. 9a. Another example of an image corrected for grayscale distortion is shown in FIG. 9b. In one aspect, the grayscale distortion may be corrected using a grayscale correction model, as shown at block 112. The model may include certain input factors to determine the amount of compensation necessary. Examples of such factors include, but are not limited to, distance from the center of the image and brightness of the image. Referring to FIG. 10, there is shown a graph of a compensation model for brightness across the field of view in order to correct grayscale distortion. An example of such a model is constructed with the optics of the imaging system to derive the compensation equations shown in FIG. 10 for brightness across the field of view. The model is constructed by using a consistent light source and a calibrated set of filters (such as 3% transmission filter (3% of the light passes through); 10.13%; 17.25%; 24.38%; 31.50; 38.63%; etc.) to arrive at curves for different brightness values. The sensor was moved using a x-y translational stage to take data points across the photosensor array.

The data points accumulated with the 9 curves shown in FIG. 10 may be fit with a curve. A $2^{nd}$ order polynomial may be used with sufficient accuracy to arrive at equations that show what the pixel value would have been if the lens distortion was minimal, which is at the center of the lens. With these equations each pixel value at each location on the sensor can be adjusted.

Figure 11A:
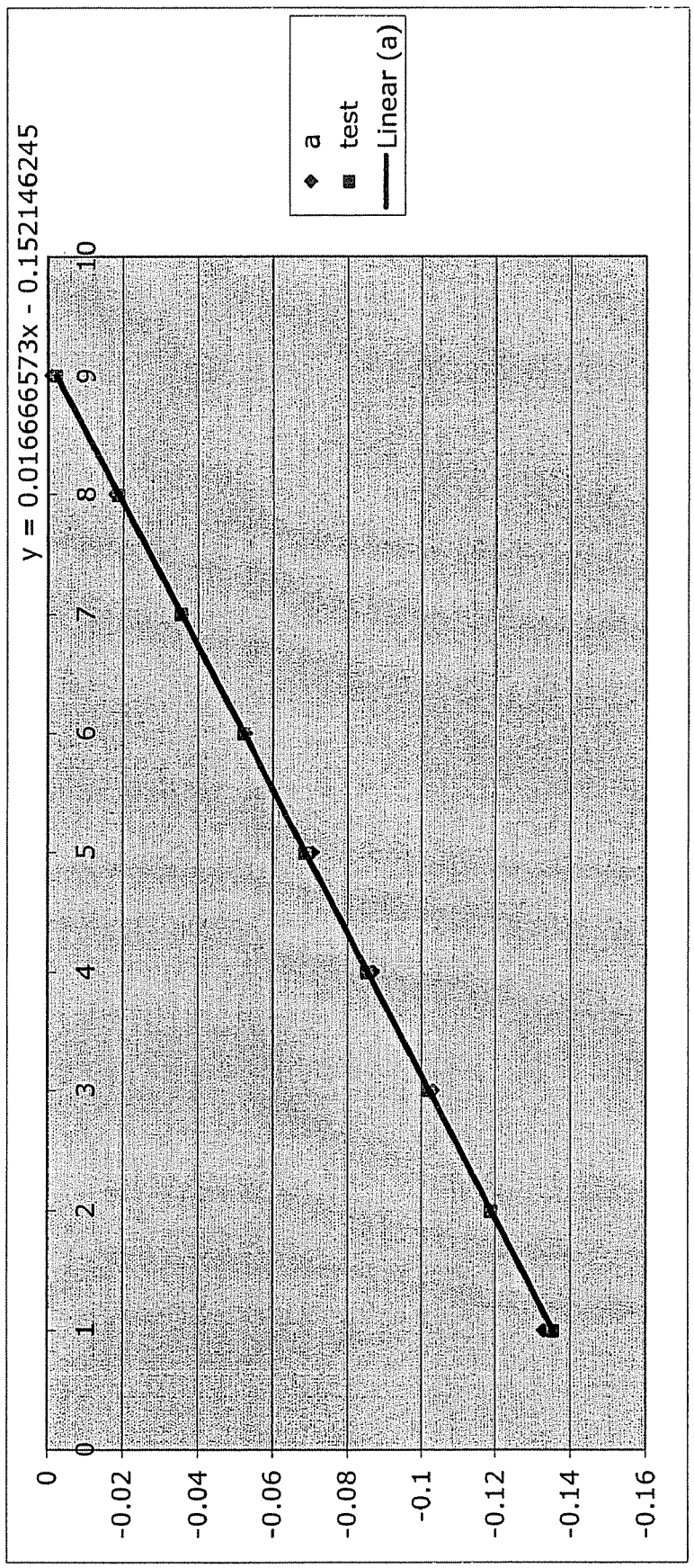
FIGS. 11a-c are graphs of constants of a second order polynomial for the compensation model of FIG. 10 with FIG. 11a showing a graph of the second order constant, FIG. 11b showing a graph of the first order constant and FIG. 11c showing a graph of the zero order constant.
Figure 11B:
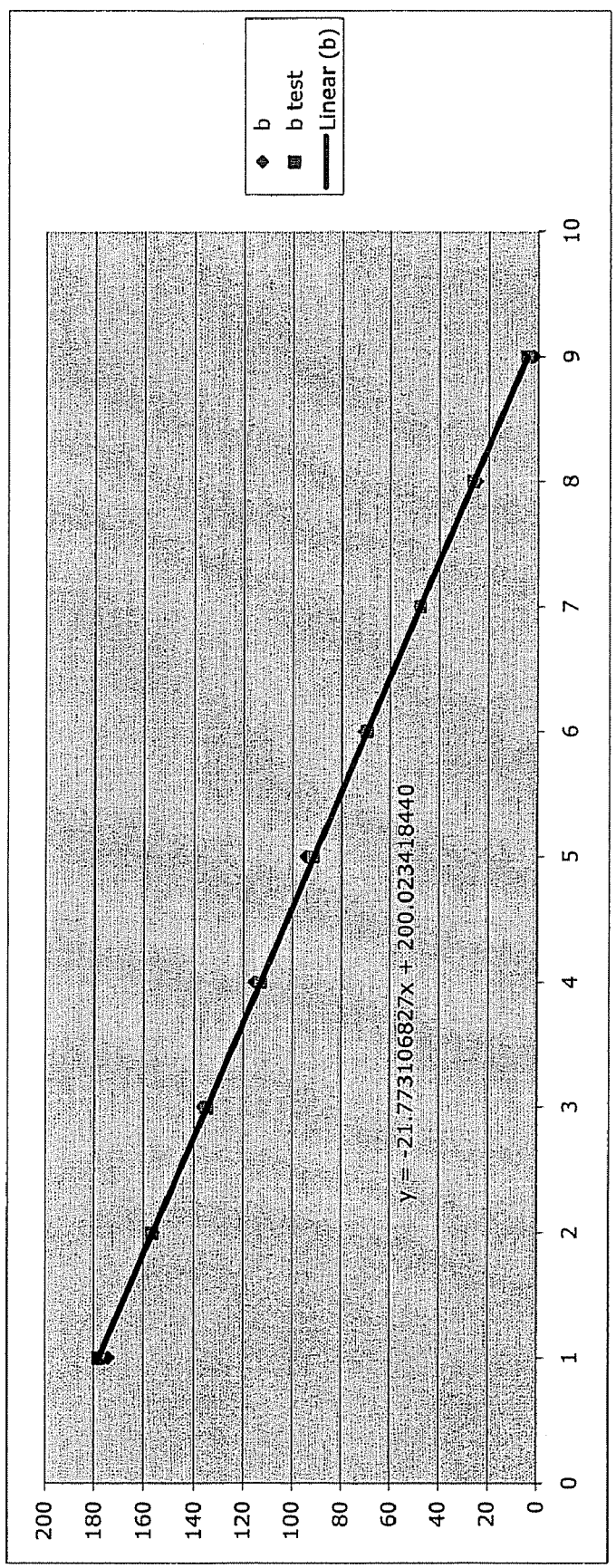
Figure 11C:
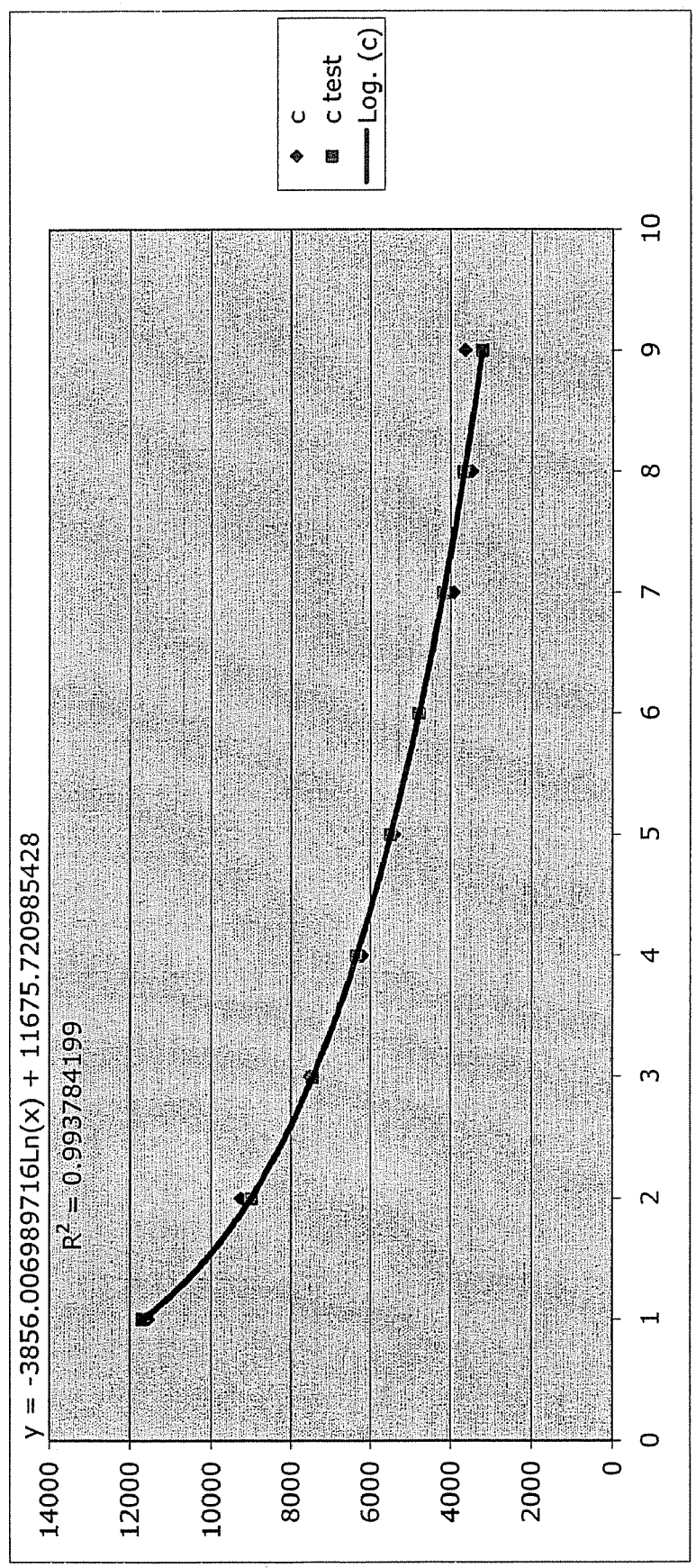

As shown in the data, the curves are a function of the brightness. The brighter the signal, the more pronounced the grayscale distortion effect on brightness. In one embodiment, one may gather a curve across the spectrum of brightness values (e.g., 65,536 for $2^{16}$). In a preferred embodiment, by modeling $2^{nd}$ order polynomial equations across the brightness spectrum, it can be determined that the $2^{nd}$ and $1^{st}$ order constants are linear and that the 0 order constants are related logarithmically. FIGS. 11*a-c* are graphs of constants of a second order polynomial for the compensation model of FIG. 10 with FIG. 11*a* showing a graph of the $2^{nd}$ order constant, FIG. 11*b* showing a graph of the $1^{st}$ order constant and FIG. 11*c* showing a graph of the $0^{th}$ order constant. Knowing these relationships, one can solve for any a, b and c given the initial position on the substrate and initial brightness value. While the curves in the model shown in FIG. 10 only factor distortion in the x-direction, the grayscale distortion model may also factor in distortion in the y-direction as well. Further, other models for compensation of grayscale distortion may be constructed as well.

Figure 12A:
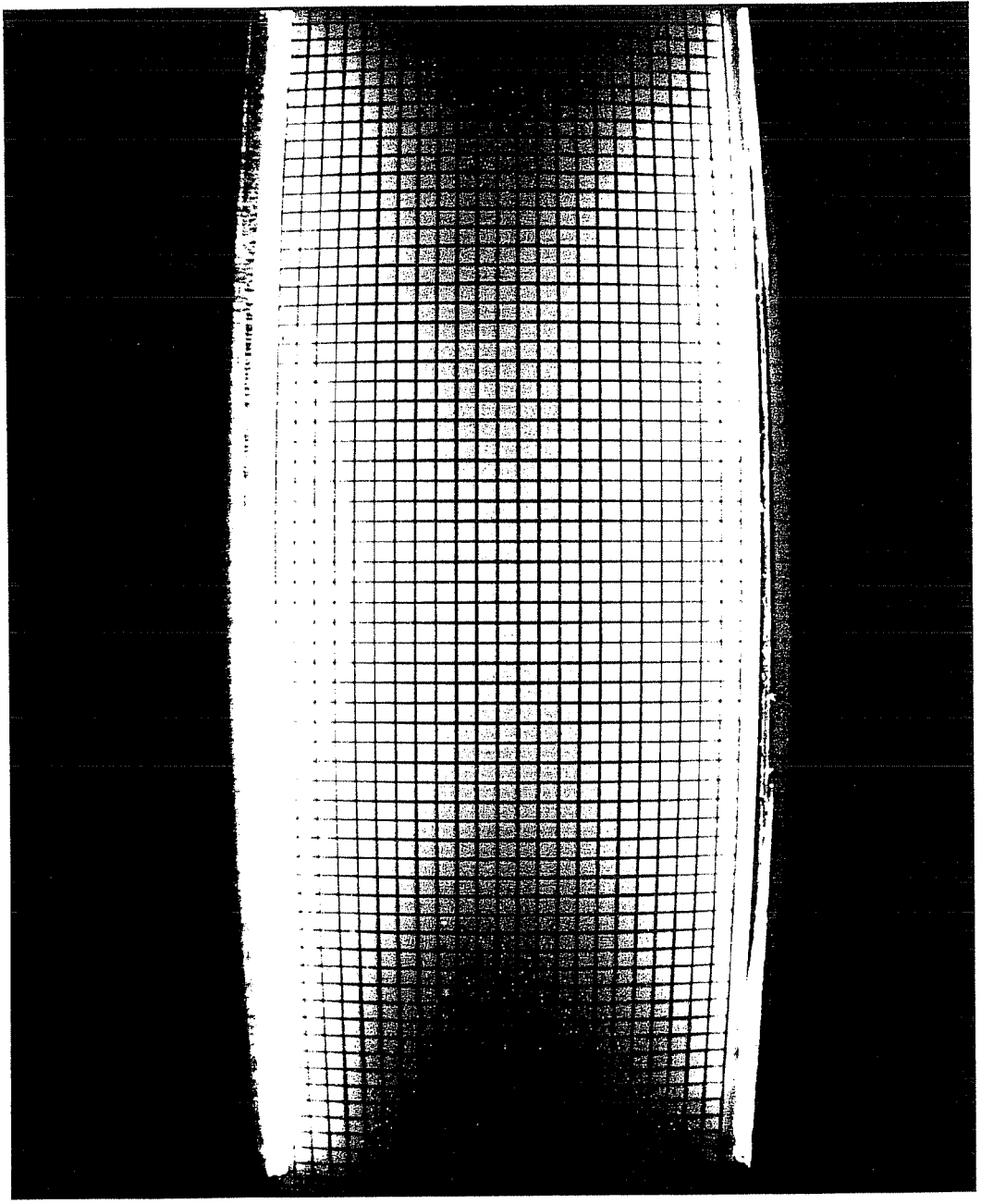
FIG. 12a is an image of a slide with spatial distortion.
Figure 12B:
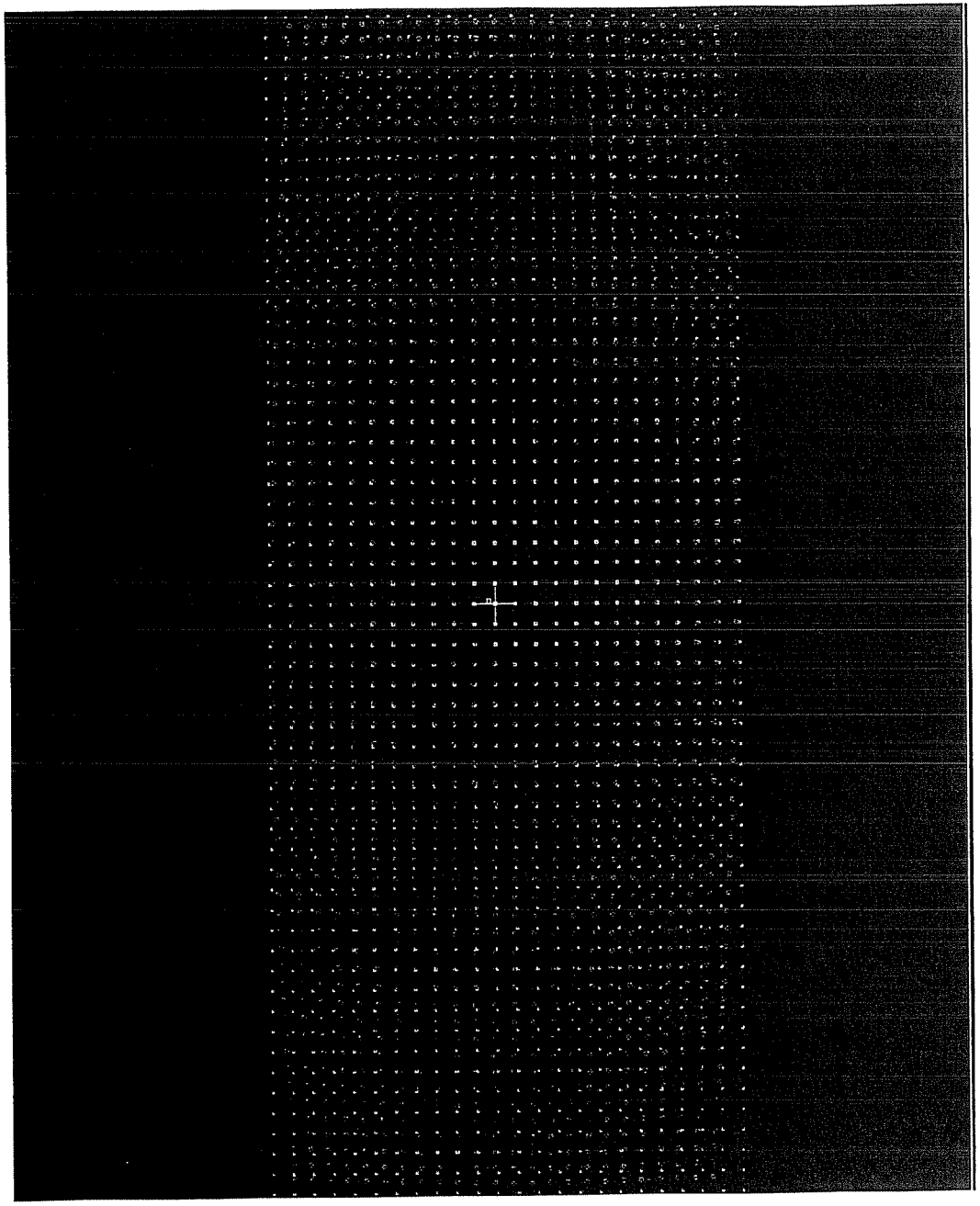
FIG. 12b is an image/printout of data in a data file that has a visual representation of the x and y translation necessary to move from the distorted point to the undistorted point is created from the image directly above.
Figure 13A:
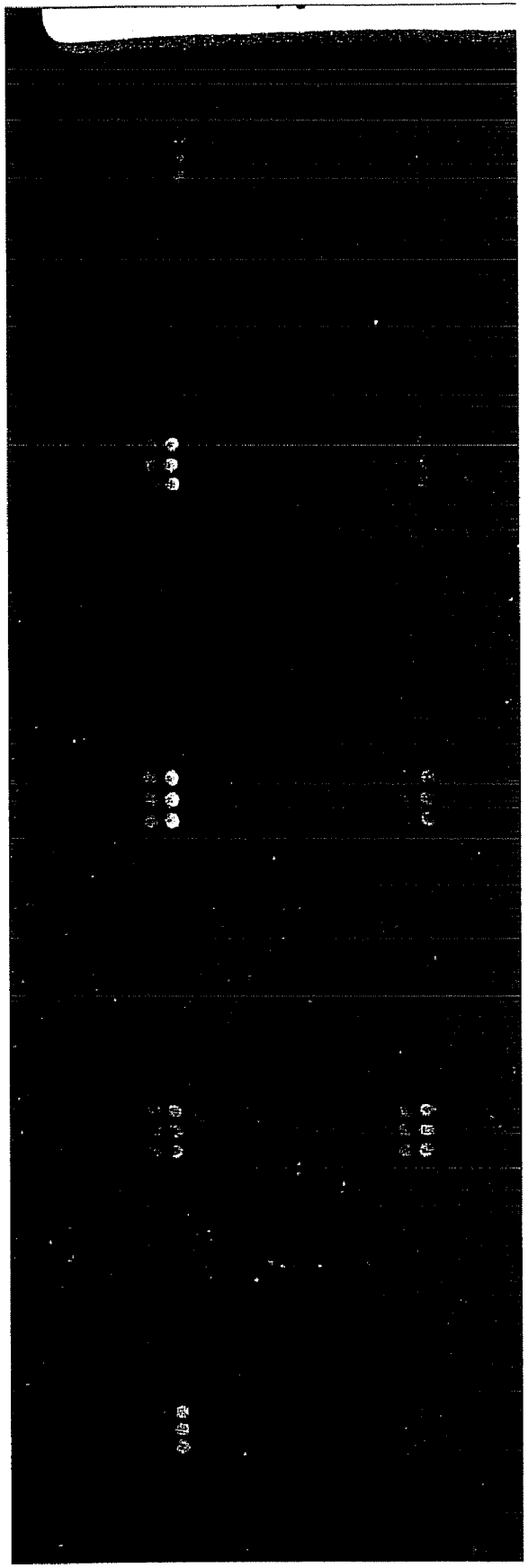
FIGS. 13a and 13b are images of a slide before and after grayscale and spatial distortion correction.
Figure 13B:
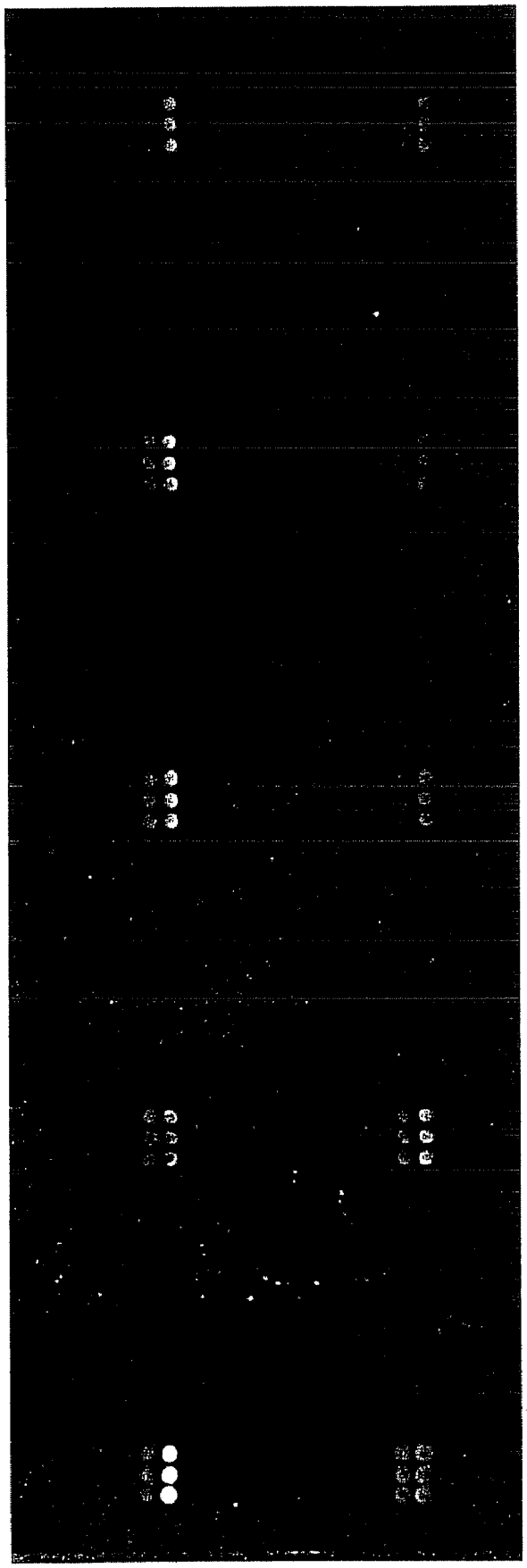

The distortion caused by the lens also causes a spatial distortion between the image and the object. The distortion is severe enough that it does not permit reliable analysis of the image. In one aspect, the spatial distortion has a negative (barrel) distortion that compresses the edges of the image, as shown in FIG. 9*a* and FIG. 12*a*. The spots at the edge are artificially smaller and thus harder to find. A model may be generated to compensate for the spatial distortion. This model may be used to correct for spatial distortion, as shown at block 114. An example of such a model is based on a calibrated grid with perpendicular lines 1 mm apart. Imaging this grid in the imaging system gives a picture of the distortion. Assuming the center of the image is undistorted, an undistorted spatial image of what the perpendicular grid of lines should look like can be created.

A data file that has the x and y translation necessary to move from the distorted point to the undistorted point is created from the image in FIG. 12*a*. Since most pixels are in between the nodes of the grid, the distortion correction procedure uses bilinear interpolation to construct a non-distorted image from the given distorted image. The input to the algorithm is a matrix of nodes, where each node describes a rectilinear bounded region of both the distorted and non-distorted images. Using the known coordinate points bounding each node, coefficients can be calculated that allows interpolation between the non-distorted points. Assuming f(x,y) is the original distorted image, and g(x',y') is the corrected image, we have the following relation:

$$x' = a_1 x + b_1 xy + c_1 y + d_1$$

$$y' = a_2 x + b_2 xy + c_2 y + d_2$$

$$g(x',y') = f(x,y)$$

Given the eight known coordinates bounding each node the eight unknown coefficients can be found. In addition to calculating the corrected coordinates, one may interpolate the grayscale value since the corrected coordinates are not integral values. Since a digital image is discrete, non-integral coordinates do not exist. Simple solutions to this problem such as selecting the grayscale of the nearest integral neighbor introduce a number of undesirable artifacts into the resulting image. On the other hand, an optimal solution such as bicubic interpolation would introduce unacceptable computational requirements. Therefore, using estimation, another bilinear interpolation is performed using grayscale values of the four nearest neighbors as in the following relation:

$$v(x',y') = ax' + bx'y' + cy' + d$$

where v is the theoretical grayscale value in the distorted image. Using the four known coordinates and the four known grayscale values, the four coefficients may be solved. Once the software has the four coefficients, it can compute an interpolated pixel value between four integral pixel values.

After the acquired image is corrected for distortion, the shapes within the corrected image should be analyzed. Shape analysis operates on the binary images, in this case the foreground objects are white and the background is black. However, the inverse is also applicable under different illumination techniques. In one embodiment, a thresholding model is used to differentiate foreground and background objects in the grayscale image in order to generate a binary image suitable for shape detection and analysis. The thresholding model attempts to find a globally applicable separation between the foreground and background objects in order to generate a simple binary image suitable for shape detection and analysis.

However, since the substrate images often contain a non-uniform background and noise irregularities due to dust, scratches, etc, as well as irregularities in illumination, a preferred embodiment employs an adaptive thresholding algorithm, as shown at block 116. Adaptive thresholding calculates the foreground/background separation based on a local neighborhood of pixel values rather than attempting to find a globally applicable separation point based on histogram analysis.

Adaptive thresholding can be modeled in a variety of ways. One such method is by the following equations, considering that the $f_{original}(xy)$ is transformed into $g_{binary}(x,y)$:

$$I_{avg} = \left(\frac{1}{(k+1)^2}\right) \sum_{i,j=-k}^{k} f_{original}(x+i, y+j)$$

$$I_\Delta = \left(\frac{q}{100} \cdot I_{avg}\right)$$

$$g_{binary}(x,y) = \begin{cases} 1 \text{ if } [f_{original}(x,y) - I_{avg}] > I_\Delta \\ 0 \text{ if } [f_{original}(x,y) - I_{avg}] \leq I_\Delta \end{cases}$$

| | |
|---|---|
| $f_{original}(x,y)$ | Grayscale input image |
| $g_{binary}(x,y)$ | Binary output image (if the particular pixel image is greater than the average pixel intensity in the specified neighborhood, the value is assigned a "1" meaning the model determines that the pixel is foreground; conversely, if the particular pixel image is less than or equal to the average pixel intensity in the specified neighborhood, the value is assigned a "0" meaning the model determines that the pixel is background) |
| $I_{avg}$ | Average pixel intensity of the specified neighborhood about the pixel f(x,y) |
| $I_\Delta$ | Pixel intensity delta. The pixel f(x,y) must exceed its neighborhood average by this delta to be considered a foreground pixel. |
| k | This variable specifies the size of the square neighborhood to be considered in the background averaging. |
| q | This variable specifies a pixel intensity delta as a percent of the neighborhood mean. |

Once the foreground pixels have been separated from the background pixels using the adaptive thresholding model, one can scan the image and identify pixel clusters that define objects. Erosion and dilation is performed, as shown at block 118, in order to remove undesirable connections between foreground objects. by separating blobs of pixel clusters connected together.

After pixel clusters have been detected and defined as single entities, blob detection builds data structures describing each cluster of connected foreground pixels as "blobs," as shown at block 120. The blob detection algorithm traverses the pixel cluster data structures and builds two additional data structures and then computes blob metrics based on the new data structures.

The blob characteristics may then calculated, as shown at block 122. These objects (i.e., the portions of the images relating to the spots) are arranged into "blobs" that allow for spatial determination to filter out noise and blobs that do not have the expected characteristics of the DNA spots. Thus, different characteristics of the blobs may be calculated so that valid DNA spots may be accepted and invalid noise may be rejected. The different characteristics including without limitation: the blob's statistical shape moments; the blob's pixel area; the blob's pixel mass (sum of pixel values); the blob's centroid coordinates; the blob's circumference; and the blob's circularity coefficient.

The blob's statistical shape moments may be found by considering the shape of the blob to represent a function of two variables and then computing statistical moments. Moments are the basis of many of the subsequent blob metrics. Moments for a continuous function $f(x,y)$ are:

$$m_{pq} = \int_{-\infty}^{\infty}\int_{-\infty}^{\infty} x^p y^q f(x, y) dx dy$$

However for a digital image, these can be summed discretely:

$$m_{pq} = \sum_{x=0}^{M}\sum_{y=0}^{N} x^p y^q f_{binary}(x, y)$$

Once the basic moments are computed, the central moments can be calculated. Central moments are normalized by the blob's location.

$$\bar{x} = \frac{m_{10}}{m_{00}} \quad \bar{y} = \frac{m_{01}}{m_{00}}$$

$$\mu_{pq} = \sum_{x=0}^{M}\sum_{y=0}^{N} (x-\bar{x})^p (y-\bar{y})^q f_{binary}(x, y)$$

When computing moments, traversal of a blob's scan segment list is used to represent the range and domain of the function $f_{binary}(x,y)$.

Another characteristic of the blob is the pixel area. The pixel area of a blob is the number of pixels in the blob. This is computed by counting the number of pixels represented by a blob's scan segment list. This value is the moment, $m_{00}$.

Yet another characteristic is the blob's pixel mass (sum of pixel values). The pixel mass of a blob is the sum of the pixel values in the blob:

$$mass = \sum_{x=0}^{M}\sum_{y=0}^{N} f_{original}(x, y)$$

where $f_{original}$ is the original 16-bit grayscale image, not the $g_{binary}$ image that has been thresholded.

Another characteristic is the blob's centroid coordinates. A blob's coordinate location is computed by using moments about the x and y axis to determine a blob's average location:

$$\bar{x} = \frac{m_{10}}{m_{00}} \quad \bar{y} = \frac{m_{01}}{m_{00}}$$

The resulting coordinates are the blob's x and y axis normalized by the blob's total area. This represents the blob's average location, or centroid.

Still another characteristic is the blob's circumference. A blob's circumference is computed by summing the distances between pixels in the blob's perimeter point list, represented by $(x_i, y_i)$:

$$c = \sum_{i=1}^{N} \sqrt{(x_i - x_{i-1})^2 + (y_i - y_{i-1})^2}$$

N is the length of the perimeter point list.

A final blob characteristic is the blob's circularity coefficient. Once the circumference and total area are known the circularity coefficient can be calculated:

$$C = \frac{c^2}{4\pi(m_{00})}$$

Where a perfectly circular blob has C=1.0. The acceptable circularity is a configurable parameter and is valid only when the blob has a certain minimum area.

Based on one, some or all of these blob characteristics, the blobs which register in the image may be analyzed and filtered to determine which are valid DNA spots and which are noise, as shown at block 124.

Well Identification

The spot detection steps provide the spots detected and the characteristics of the spots detected (such as area, circumference, etc.). Based on this, at least some of the detected spots are analyzed (and preferably geometrically analyzed) to determine, from the unordered collection of detected spots how the spots are organized into wells and rows.

Well identification takes the unordered collection of spots which have been detected (as discussed in the previous section) and attempts to automatically identify the spots which compose a well. This automatic identification does not require human operator intervention, as is required in prior art devices. Rather, the identification of the wells is based on attributes of the detected spots (such as spacing, patterns, etc.).

As discussed above, a substrate may be composed of a plurality of wells. Each of the wells may contain at least two spots (and preferably a plurality of spots). The spots within a certain well typically comprise one experiment so that the spots are related to testing for a particular target or series of targets. Well identification analyzes certain features of the detected spots, such as spacing between some or all of the detected spots, patterns for the detected spots, etc. in an attempt to obtain attributes about the well, such as the number of spots within the well, the location of the spots within the image acquired (e.g., in the case of pixels, which pixels groupings correspond with a particular spot), the geometry of the well, etc. A typical example of a well is a matrix of spots. The matrix may contain 3×3 spots (for a total of 9 spots in the well), 4×4 spots (for a total of 16 spots in the well), etc. depending on the particular substrate. For example, FIG. 14 shows a substrate with ten wells, each well containing spots.

The attributes in a well may be derived by analysis of the detected spots and/or by comparison of know characteristics of wells. In one aspect, the unordered spots are analyzed to determine the positive control spots within the wells. In a second aspect, dynamic measurement of spot to spot distances is used to differentiate spots within a well and differentiate spots within different wells.

Figure 6:
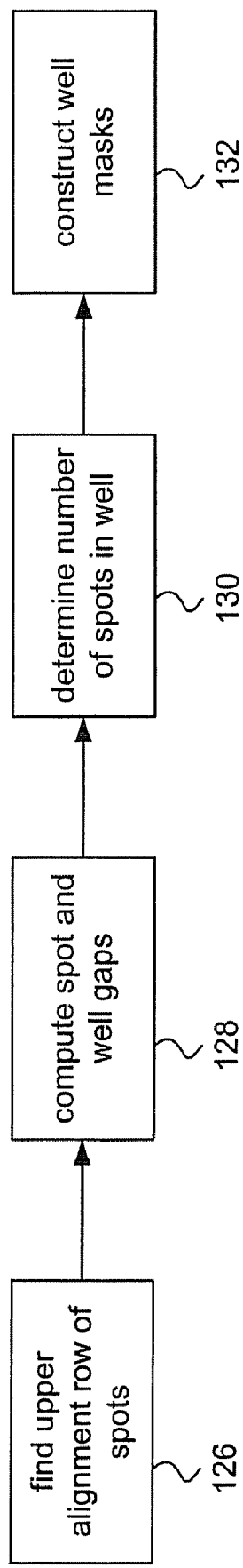
FIG. 6 is a flow chart of one embodiment of well identification on the substrate, as discussed in FIG. 4.

Referring to FIG. 6, there is shown a flow chart of one embodiment for identifying wells on a substrate. In a preferred embodiment, at least a portion of the spots detected are analyzed. For example, when an experiment uses positive control spots, the detected spots are analyzed to determine the positive control spots. Based on a predetermined knowledge of the location of the positive control spots, the software may search for these spots in identifying the wells. In a preferred embodiment, the positive control spots are located in the upper row of each of the wells. For example, as shown in FIG. 14, all of the spots in the upper row of each of the wells is a detected spot. Thus, the upper alignment row of spots is first determined, as shown at block 126. Geometric analysis may be used to find the topmost row of spots in each well in a row of wells. This row of spots should form roughly a line from left to right. Since other requirements dictate that spots other than those in the topmost row of each well may or may not be visible, the software in a preferred embodiment only searches for the topmost row. The topmost row of each well is called the alignment row because it is guaranteed to exist and be visible and can be used to make geometric assumptions about other spots in a well that may or may not be visible. All of the alignment rows of each well in a horizontal row of wells from roughly a line of spot patterns that can be targeted by the software. This line, for example, is drawn across the upper rows in FIG. 14. Thus, by analyzing the detected spots within different wells, the automatic detection of wells is based on locating non-random groups of spots within different wells that form a discernable pattern along a line of intersection from left to right.

Searching for an aspect of a well, such as an alignment row, follows the image analysis described above except that the aspects of the well deal with objects of a higher abstraction than the image processing. When the spots are defined in the image as detected "blobs," the current set of all detected blobs may be filtered based on blob characteristics, such as blob area and blob circularity. Based on predetermined characteristics, the range of acceptable values of the blobs is configurable. This filtering removes blobs that are not likely to be valid hybridized spots. This is efficient and effective for subsequent processing that the data set is not too populated with extraneous objects that may randomly generate unintentional patterns.

Blobs that meet the predetermined filtering criteria for hybridized spots are collected into a new data set that represents the current set of probable hybridized spots, called the Total Spot Set. Once the Total Spot Set has been determined, an artificial image is constructed called the Indexed Intersection Image ($I^3$). The software artificially renders the spot shapes into the $I^3$ image using each spot's index value as the constituent pixel values. The $I^3$ image allows the software to efficiently calculate intersection sets between spots and lines.

The forward row scan may begin at any aspect of the acquired image. In a preferred embodiment, the forward row scan begins at the top of the image and proceeds down toward the bottom of the image. The row scan first attempts to locate the alignment spot row for the upper row of wells and then attempts to locate the alignment spot row for lower rows of wells.

Once the upper alignment row has been properly located, the search for the lower alignment well may be aided by heuristic calculations that can be performed based on characteristics of the upper alignment row. The basic unit of computation in the forward row scan is the Spot Set. The Spot Set is initially defined by traversing a virtual line from the left edge to the right edge of the $I^3$ image and collecting the intersected spots. The forward row scan moves forward by a specified number of pixel rows as long as the resulting spot set is empty. Once the initial spot set is non-empty, an iterative convergence may be performed to refine and raise the quality of the linear intersection of the spot set.

Several methods of spot set convergence may be used. Two example methods include a static method and a line-fit method. The line-fit method is able to tolerate a higher degree of variability in the input image. However, the line-fit method of convergence, by itself, may be unstable. The static convergence method does not tolerate a high degree of variability but it is very stable. Therefore, it is preferable to use static convergence of the spot set and then attempt to refine the spot set with the line-fit convergence. This combination produces an acceptable compromise between tolerance of variability and stability.

In static convergence, the software considers the spots to intersect a line with the equation y=mx+b but does not attempt to modify m, only b is modified. Additionally b is only modified such that it can increase, never decrease. In order to statically converge, the average y centroid of the current spot set is computed and then assigned a new b term as follows:

$$b_{new} = -m\left(\frac{I_{width}}{2}\right) + b_{current}$$

where $I_{width}$ is the width of slide image in pixels. A new spot set is defined by the intersection of the new line. The process is iterated until two adjacent iterations produce identical spot sets.

In line-fit convergence, the software considers the spots to intersect a line with the equation y=mx+b and attempts to adjust both m and b to properly converge the spot set. In order to perform a line-fit convergence, the software performs a least-squares line-fit on the centroid coordinates of the current spot set. The resulting line is used to define a new spot set. The process is iterated until two adjacent iterations produce identical spot sets. When attempting to line-fit converge, the software considers a configurable range of valid line slopes. The convergence is aborted if this slope range is exceeded. If the line-fit convergence is aborted the spot set produced by the static fit is chosen as a fallback and the processing continues as normal.

After the spot set has been refined and stabilized by the convergence iterations, a qualitative analysis of patterns present in the spot set is performed. To analyze the spot patterns, the software considers that the spot set is not unordered but rather represents spots intersecting along a line from left to right. As discussed above, known characteristics of the well may be analyzed to make conclusions regarding the unordered spots. Two characteristic elements of this linear spot pattern are the empty gaps between spots and the spot themselves. Analysis of the characteristic elements may take a variety of forms. One such form is to transform the spot set into an abstract symbolic from that facilitates symbolic pattern matching.

As shown at block 128, the spot and well gaps are computed. One of the fundamental elements of the spot set pattern is the gaps between spots along a line. The software may collect at least some (and preferably all) of the gap distances and attempts to group them into Gap Classes. A Gap Class is collection of distinct, measured, inter-spot gaps that are statistically similar such that they can be considered the same.

Based on the gaps computed, the number of spots within a well and/or the well pattern is determined, as shown at block 130. For example, based on the gaps computed, the layout of the particular well (number of spots, distribution of spots within well, layout, etc.) may be determined. To accomplish this, gaps are collected, coalesced using heuristics into classes, sorted, and then assigned symbols according to each gap class's frequency of occurrence along a line. The inter-spot gaps themselves are not assigned symbols, but rather each gap class is assigned a symbol. The symbols are represented by the letters a to f.

The most frequently occurring gap class may be assigned a, the next most frequently occurring gap class is assigned, b, and so on. A number of heuristics may be used while assigning gap class symbols to protect against erroneous spot sets.

On a properly formed alignment row, the gaps between spots in a well's alignment row should be the most frequently occurring gap class, that is represented by the symbol a.

Once the gap class symbols have been assigned, they can be combined with the other fundamental element of the linear spot pattern, the spots themselves. Spots may be represented by the symbol S. Each actual inter-spot gap may be represented by the symbol corresponding to the gap class to which the actual gap belongs.

A linear spot pattern transformed into symbolic form may look similar to this example:

cSaSaSaSbScSdScSaSaSaScSaSbScSaSaSaSb

The above example symbolic form represents a group of three wells each consisting of four spots across. The form also shows various extraneous spots, i.e., noise, that occurred in the linear spot set.

After the spot set has been transformed into symbolic form, the software may use a pattern matching mechanism based on regular expressions to determine if the current spot set represents a valid alignment row. The regular expression used to match an alignment row is configurable and contains definitions of subgroups that are used to delineate symbolic subsets that define each well.

During the building of the data structures representing spots, spot sets, gap classes, and the symbolic form of a linear spot set, the software maintains links between the various abstractions. These links enable backward traversal such that from the substring found by the regular expression matching, the software can determine the set of actual spots represented by the substring based on each symbol's string index.

Assuming the following regular expression:

(SaSaS)(aS)+ pattern matching will deconstruct the example symbolic spot set as follows:

C(SaSaSaS)bScSdSc(SaSaSaS)cSaSbSc(SaSaSaS)b

The parenthetical subgroups each represent a detected well.

For a valid alignment row, the software uses the links maintained between the abstractions to build a data structure representing spot clusters. Each spot cluster represents a group of spots horizontally along a line from left to right that make up the alignment row for one well. A detected well is defined by characteristics derivable from the well's spot cluster.

If the spot set is not a valid alignment row, then the software advances the current forward row scan past the current spot set and continues again to converge on another spot set. Advancing the current forward row scan past the current spot set is done by advancing the b term of the line equation without adjusting the m term. The b term is increased until two adjacent iterations produce different spot set.

Based on the determination of the number of spots in a well, a well mask is constructed, as shown at block 132. In the instance where an alignment row has been found, the software uses the metric data from actual spots in the alignment row to construct a mask of expected spots for each well. For example, where it is predetermined that the well's geometry is assumed to be square, there are as many spots down as there are spots across in the alignment row. In particular, if it is determined that the well is a 3×3 well based on pattern matching and if the alignment row (top three spots) have been found, the two lower rows may be found since the software knows that the two lower rows will line up, with three spots each, below the upper alignment row.

For each spot in an alignment row, a column of spot masks are interpolated underneath. When computing the vertical column of spot masks the software takes into consideration the linear equation representing the entire alignment row across the slide. The circular diameter of the interpolated spot masks is based on the average diameter of the alignment row spots of the entire slide.

Each interpolated spot's location is calculated as follows:

$$\theta_{mask\_column} = \tan^{-1}\left(\frac{-1}{m}\right)$$

$$y'_i = y'_{i-1} + \overline{D}|\sin\theta|$$

$$x'_i = \begin{cases} x'_{i-1} + \overline{D}\cos\theta & \text{if } (m < 0) \\ x'_{i-1} - \overline{D}\cos\theta & \text{if } (m \geq 0) \end{cases}$$

where $(x'_i, y'_i)$ is the centroid coordinate of each interpolated mask spot and $\overline{D}$ is the average spot-to-spot distance between spots on the entire alignment row. Note that $(x'_0, y'_0)$ is the centroid coordinate of the alignment row spot. Thus, based on the finding of an alignment row and based on the pattern matching, the software determines each of the spots within the wells. For example, FIG. 14 shows the detected spots in the wells by circles which are drawn for the upper alignment row and circles also drawn for spots determined based on the alignment row.

Spot Quantification

Figure 15:
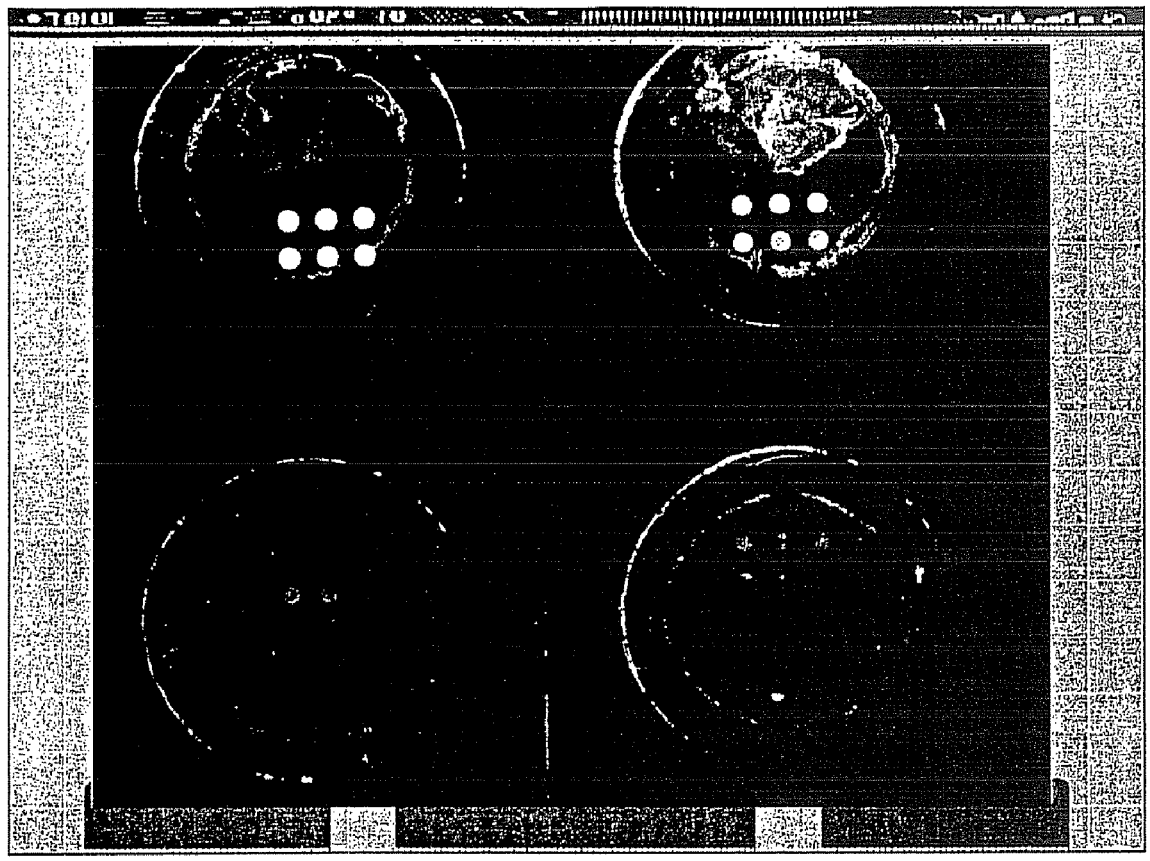
FIG. 15 is a photograph of a set of samples with a particular exposure time for the photosensor.

After the wells are identified, the individual spots within the wells are quantified. For example, the photosensor used to detect nanoparticles may saturate, limiting the amount of information which may be obtained from the image. An example of this problem is illustrated in FIG. 15 which shows a photograph of a sets of samples with a particular exposure time for the photosensor. FIG. 15 demonstrates the inherent limitations of a photosensor. The photosensor obtained this "snapshot" of the test using a fixed set of parameters (i.e., one exposure time). Because of this, the data which may be extracted from the different sets of samples is limited. For example, the data extracted from the samples in the upper left of FIG. 15 are limited since the photosensor is in complete saturation. Similarly, the samples in the lower right and lower left regions of FIG. 15 provide limited data since the light has not registered yet. Only the samples in the upper right portion of FIG. 15 provide optimal data extraction. This is due to the fact that the photosensor is in the dynamic range of the sensor (i.e., light has registered but not to the point of significant saturation). Thus, this "snapshot" shown in FIG. 15 only provides limited data, seriously undermining the ability to images with large variations in reflected light which can frequently occur when imaging DNA hybridization spots.

In order to extract usable information from the samples, the dynamic range of the sensors must be increased to allow for more useful information to be obtained in an area of interest within an image. This increase in the dynamic range is achieved by controlling the amount of electromagnetic radiation which is registered by the sensor. As discussed previously, in a preferred embodiment, controlling the amount of electromagnetic radiation registered by the sensor may be accomplished by modifying parameters which control the light incident on the sensor, such as exposure time, aperture size, etc. Moreover, other parameters which affect the amount of light registered on the sensor may be used. The data is then obtained based on the modified parameters of the sensor (e.g., different exposure times), as discussed subsequently in more detail. The data is subsequently analyzed in order to detect registration of nanoparticles, as discussed in the subsequent section.

Examples of data which may be obtained by modifying the amount of light registering on the sample are shown in FIGS. 16*a*-16*d*. Referring to FIG. 16*a*, there are shown three spots within a well (for example, one positive control test spot 164, one negative control test spot 166 and one target test spot 168). As discussed above, a well is an organizational method wherein a group of experiments can be placed together and a decision can be reached by reading some or all of the information in a well. The sensor registering the wells in FIG. 16*a* has a short exposure time; therefore, the sensor registers no or minimal intensity (the spots are black). FIGS. 16*b* to 16*d* lengthen the exposure time of the sensor, thereby allowing more light to transmit to the sensor. As shown in FIG. 16*b*, the positive control test spot and the target test spot begin to register (are the color gray), whereas the negative control test spot remains black. The exposure time is again increased in FIG. 16*c*, so that the positive control test spot and the target test spot are in saturation (are white) whereas the negative control test spot begins to register intensity. The exposure time is increased again in FIG. 16*d* so that all three spots are in saturation. The series of Figures show both the limitations of the sensors and the potential for extracting useful information. For the example shown in FIGS. 16*a*-16*d*, one may conclude either by examining FIG. 16*b* or 16*c* that the target test spot is a positive test spot based on the comparison of the target test spot with either the positive control test spot or the negative control test spot.

Alternatively, as shown in FIG. 17, the analysis of the target test spot may be performed in a different manner. There are shown five control spots 170 and a target test spot 172. The parameters which affect the light registering on the sample may be modified such that the target test spot may be in the dynamic range of the sensor. For example, the exposure may be modified such that the target test spot may either be near or at the beginning of saturation of the sensor. The target test spot may then be compared to the control test spots and a determination may be made based upon the comparison. FIG. 17 shows a total of five control spots; however, less or more control spots may be used. As shown in FIG. 17, the target test spot is most nearly like the second control spot from the top.

As shown in FIGS. 16 and 17, the dynamic range of the sensor may be adjusted automatically by adjusting the sensor's parameter's, such as the exposure time. In a preferred embodiment, an area of interest in the image, such as a well, may be analyzed using different exposure times. For example, FIG. 14 shows areas of interest that are drawn as squares around the spots within a particular well. The various exposure times may be taken between the dark level to the saturation level (or just at saturation) in the area of interest. In this manner, the sensor operates in its linear range, thereby providing increased useful data in which to analyze the spots within the wells and/or also the spots between the wells.

Figure 7:
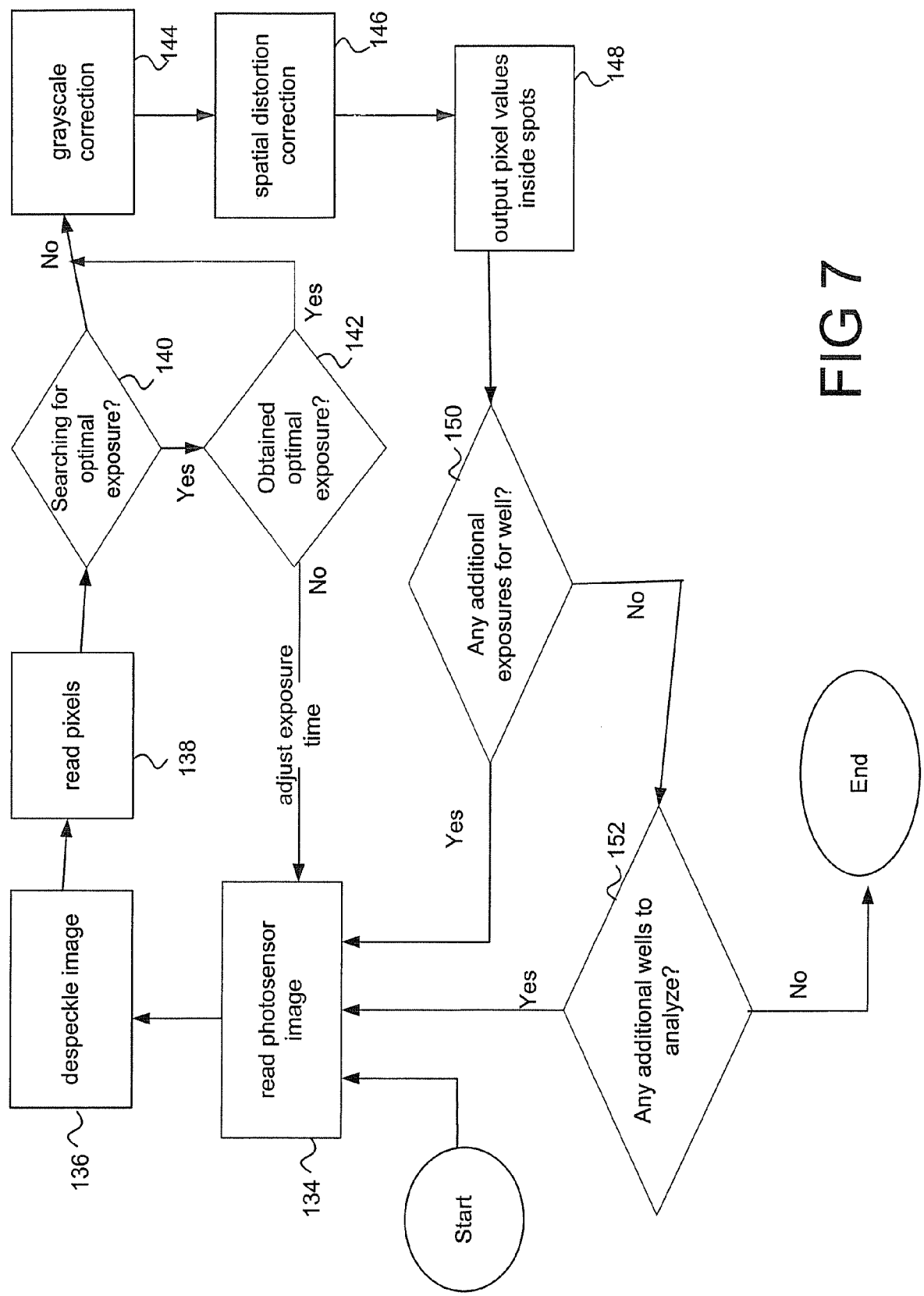
FIG. 7 is a flow chart of one embodiment of spot quantification on the substrate, as discussed in FIG. 4.
Figure 8:
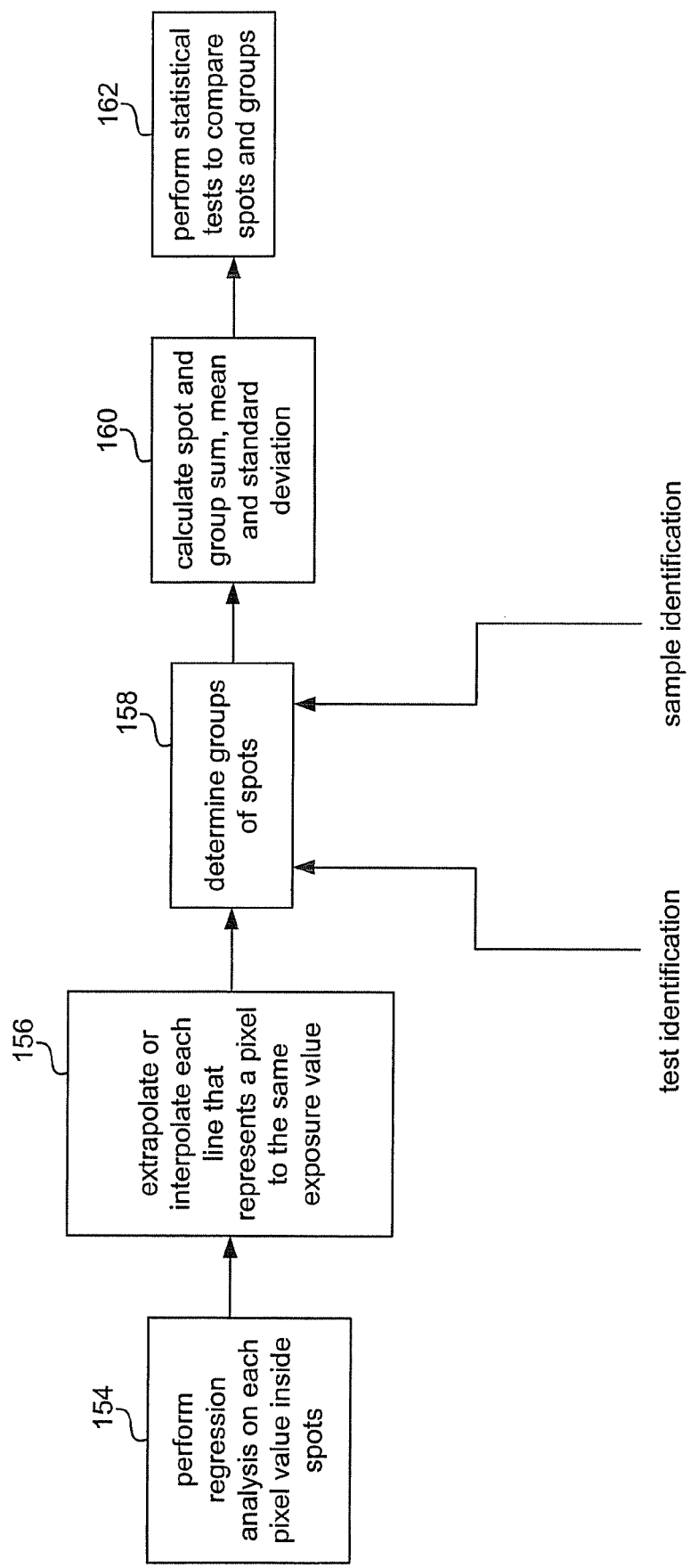
FIG. 8 is a flow chart of one embodiment of decision statistics, as discussed in FIG. 4.

Referring to FIG. 7, there is shown a flow chart of one embodiment of spot quantification on the substrate. In one embodiment, the image is divided into different areas (e.g., different wells which were identified in the well identification process). Images are then taken at different exposure times for the different areas. As shown at block 134, the image is acquired by reading the photosensor image. Optionally, the image may be filtered, such as by despeckling, to remove dirt, dust, etc. from the image, as shown at block 136. This step is similar to the despeckling step (at block 108) in FIG. 5.

The image is then read, as shown at block 138. In this step, the portion of the image which is the current area of interest is read. For example, if well #1 was the first area of interest, the pixel values for well #1 (as determined in the well identification process) is read. As shown in FIG. 14, the intensity and clarity of wells on the substrate vary based on where the well is located. For example, the intensity/clarity of well 2 is different than that of well 5. Thus, focusing on an area of interest, such as a particular well, may assist in processing.

Then, it is determined whether an optimal exposure is sought, as shown at block 140. Before obtaining multiple exposures for a particular area of the substrate, it is preferred that an "optimal" exposure time be obtained. The "optimal" exposure time, as discussed above, may be defined as the amount of electromagnetic radiation registered by the sensor which, based on the sensor's characteristics, may best enable the detection of spots on the substrate. In the current example, the "optimal" exposure time may further be defined as being at or nearly at the outer boundary of the linear range of the sensor. In a preferred embodiment, the outer boundary of the linear range of the sensor may be quantified as a percentage saturation of the image. For example, the read pixels may be analyzed to determine if the optimal exposure time has been obtained, as shown at block 142. Specifically, the read pixels are analyzed to determine if a certain percentage (such as 1%) of the pixel values are at the saturation value. Based on the percentage determined, the exposure time is either increased (if less than the desired amount of pixels are saturated) or decreased (if more than the desired amount of pixels are saturated). After an optimal exposure time is found, the image may optionally be subject to correction due to grayscale and spatial distortion, as shown at blocks 144 and 146. These correction models were discussed above with respect to blocks 112 and 114 of FIG. 5. Thereafter, the corrected pixel values inside the spots in the certain area of interest are output, as shown at block 148.

Since multiple exposures are sought in the linear range of the sensor, it is inquired whether additional exposures for a particular area (such as a well) are sought, as shown at block 150. For example, if four exposures are sought in the linear range and the "optimal" exposure was 100 mSec, three additional exposures are obtained for the area of interest at 25 mSec, 50 m Sec, and 75 mSec. It is therefore preferable that the exposure times are evenly distributed within the range of 0 to the optimal exposure time. Alternatively, different exposure times may be selected within the range of 0 to the optimal exposure time. The system then iterates for the particular area of interest for the different exposure times. After all of the exposures are obtained for a certain area of interest, as shown at block 150, it is inquired whether there are any other areas of interest (i.e., any other wells to be analyzed), as shown at block 152. If there is another area, the program is repeated by first obtaining an optimal exposure for the area of interest, and then obtaining images at different exposure times.

Figure 18:
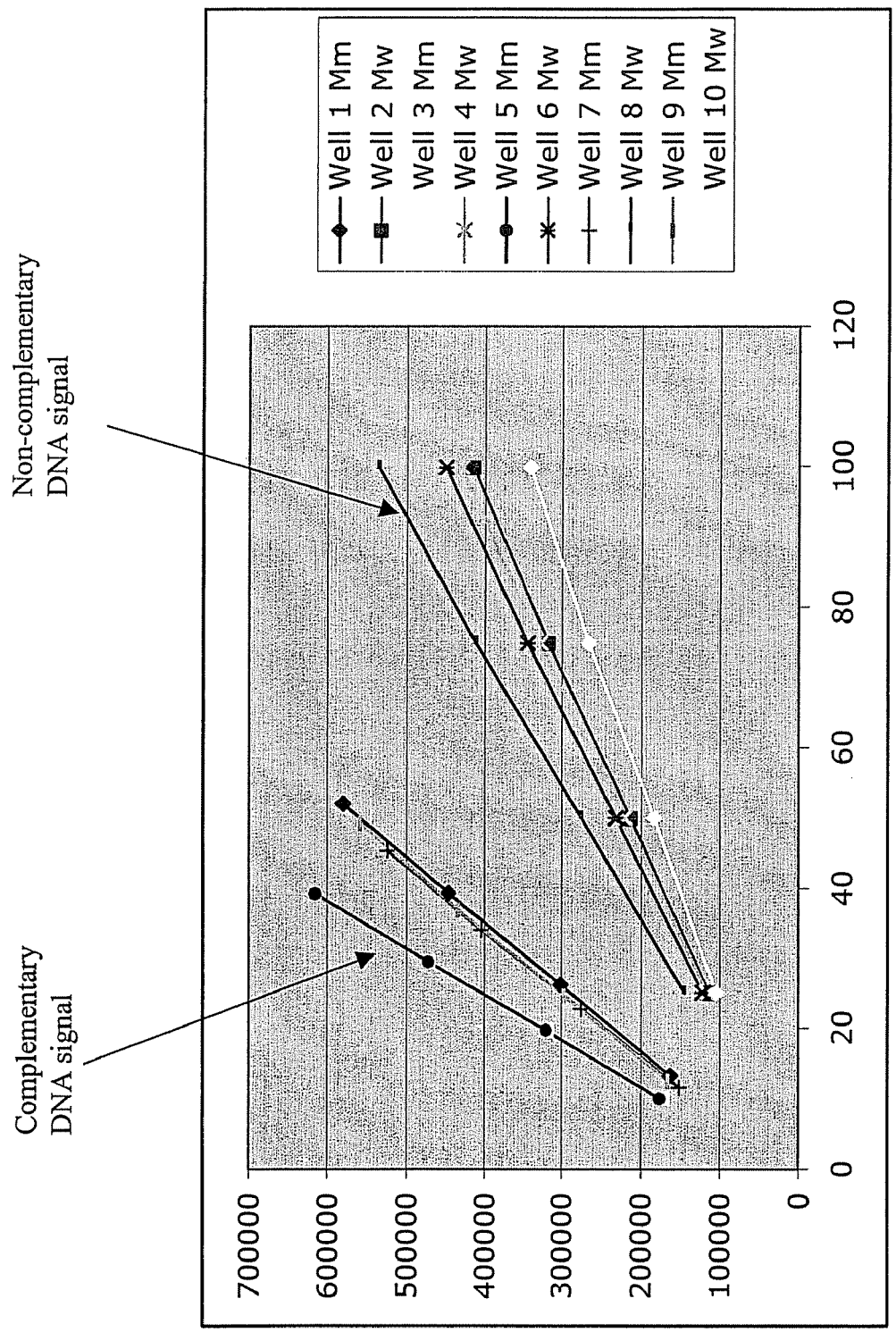
FIG. 18 is a graph of experimental data for multiple exposure times versus pixel values for various wells on a slide.

Referring to FIG. 18, there is shown a graph of experimental data for multiple exposure times versus pixel values for various spots within the wells on a slide. The x-coordinates are time in mSec and the y-coordinates are summation of pixel values. For example, the results for a row of spots for each of the ten wells on the slide are shown. As shown in the Figure, a wide range of exposure time (10-100 mSec) is necessary to obtain meaningful data from the image. Thus, focusing on a particular area of interest and acquiring images of different exposures within the area of interest assists the spot quantification.

Decision Statistics

Decision statistics analyzes the results of the spot quantification to determine conclusions.

Based on the output pixel values for the various spots, a "derived" pixel value may be determined by the regression analysis for a predetermined exposure time. In a preferred embodiment, the "predetermined" exposure time is chosen as the longest "optimal" exposure time. Other exposure times may be chosen for the predetermined exposure time. Based on this longest "optimal" exposure time, "derived" pixel values may be determined for each pixel within a well.

Figure 19:
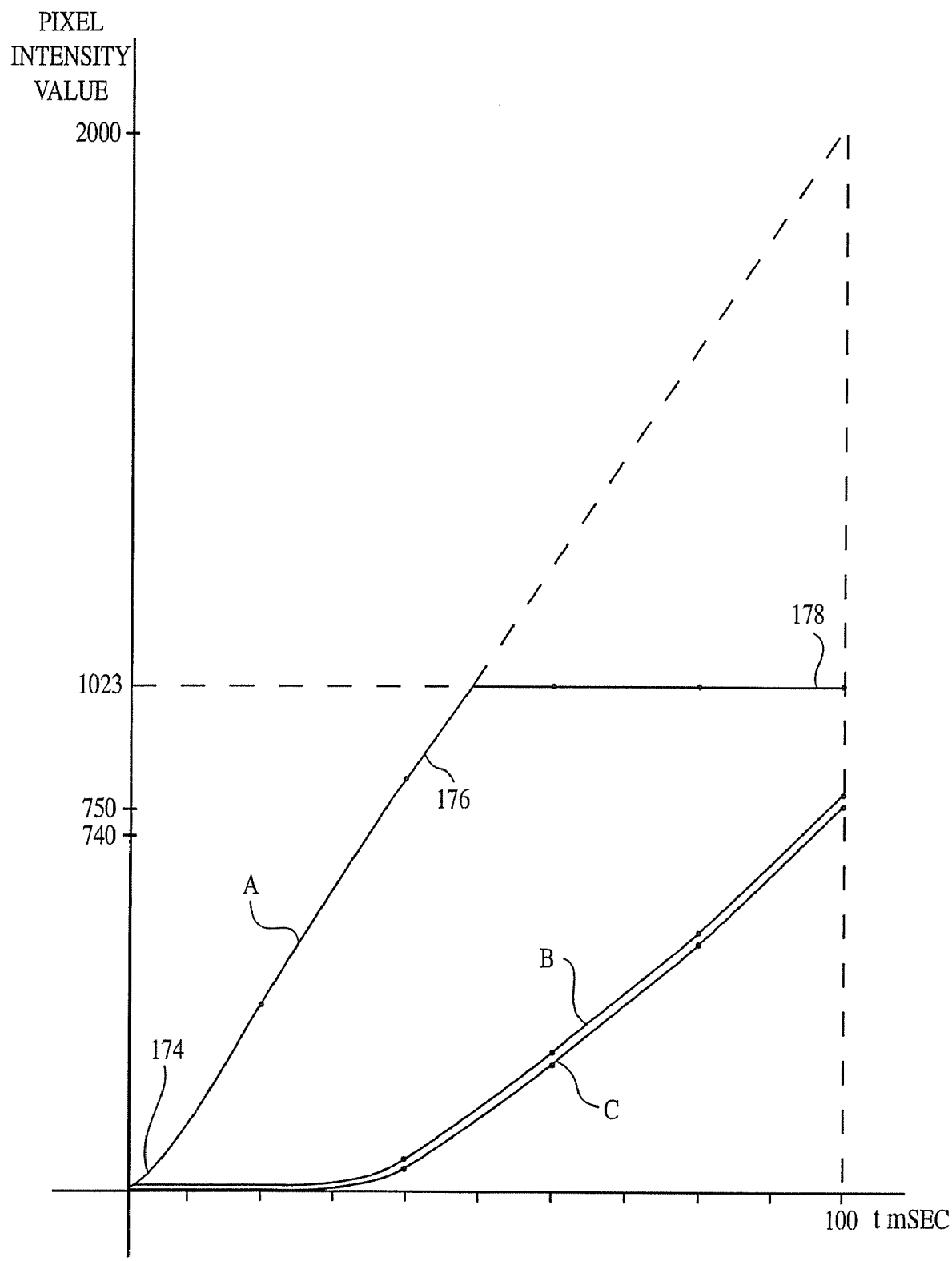
FIG. 19 is a graph of exposure time versus pixel intensity value registered by a sensor for a spots within one well on the substrate.

An example of the derived pixel values is shown in FIG. 19, which has on the x-axis exposure time (t) and on the y-axis pixel intensity value (I). As shown in the graph, there is a first portion of the graph 174 wherein the exposure time is very small and wherein the pixel value intensity is small. These exposure times indicate that the sample has not appreciably started to register on the sensor. There is a second portion 176 in the graph wherein the intensity begins to increase and wherein useful data may be obtained. There is a third section 178 wherein the intensity begins to level off. This third section 178 is where the sensor is in saturation and where useful data is limited.

The values shown in FIG. 19 correspond to spots within a particular well. As discussed above, the optimal exposure time is preferentially determined based on a section of the image (such as a portion of the image for the entire well, such as the box drawn around the well in FIG. 14). Once the optimal image is determined, different exposures which are preferentially less than the optimal exposure are taken. For example, if the optimal exposure is 100 mSec, four different exposures at 20 mSec, 40 mSec, 60 mSec and 80 mSec may be taken. Curve "A" are readings for one pixel within a positive control test sample within the particular well for the five exposures. Curve "B" are readings for one pixel for a target test sample within the particular well for the five exposures. Curve "C" are readings for one pixel for a negative control test sample within the particular well for the five exposures. The pixel intensity value (I) for exposure time (t=100 mSec) for curve "A" is in the third section 178 of the target well and is a value of 1023. The value in the saturation region (1023 in FIG. 19) is not worthwhile for comparison since the sensor is has stopped registering additional intensity. In order to compare the data, the pixel intensity value in the saturation region should be modified. In one embodiment, this is performed by a regression analysis on each pixel value inside the spots, as shown at block 154 and then extrapolating or interpolating a curve that represents all the pixels at the same exposure value, as shown at block 156.

In one embodiment, the intensity for an exposure time is determined based upon the function of the curve which is fit to data points in the second region 176. For example, to determine the intensity of the control sample, the value is extrapolated based upon the values in the second portion of the graph. This is shown by the dotted line in FIG. 19 which shows modified value for the Intensity (approximately 2000 in FIG. 19). This extrapolation may take the form of a linear extrapolation, as shown in FIG. 19. Alternatively, a curve may be fitted to the second portion of the graph and thereafter this curve may be extended to the exposure time of interest in order to determine different intensities. The values at t=100 mSec for curves "B" and "C" do not require extrapolation since deep saturation has not occurred. Therefore, the values may be read directly from the readings (750 and 740 for curves "B" and "C," respectively) or may be interpolated. Thus, the pixel intensity values for a predetermined exposure time may be derived (either by extrapolation or by interpreting the data points) for each pixel in an area.

The groups of spots in the well may be determined as target, positive control or negative control based on information supplied, such as test and sample identification, as shown at block 158. This step of determining the groups of spots may be performed before or after the regression analysis in block 154, the extrapolation/interpolation in block 156 and/or the calculations in block 160.

From these derived pixel values, a statistical analysis may be performed to determine whether the target spot is more like the control positive or control negative spot. Tests for infectious diseases where the outcome would be a positive result or negative result might use such an embodiment. Alternatively, the target spots can be compared directly to one another. Tests for genetic dispositions where the outcome is wild type, mutant or heterozygous might use direct comparisons of various target spots. The spots may be compared based on a summation of all of the derived pixels in a spot, an average value for the derived pixels in a spot, and the standard deviation for the derived pixels in a spot, as shown at block 160. From these values, statistical tests such as differences between means (t-Test, z-Test, etc.) may be performed, to compare spots and groups of spots, as shown at block 162. Alternatively the spots could be compared to each other with a percentage difference calculation or a ratio calculation.

Preferred embodiments of the present invention have been described herein. It is to be understood, of course, that changes and modifications may be made in the embodiments without departing from the true scope of the present invention, as defined by the appended claims. The present embodiment preferably includes logic to implement the described methods in software modules as a set of computer executable software instructions. A processor implements the logic that controls the operation of the at least one of the modules in the system, including the illumination module, the power module, the imaging module, and the input/output module. The processor executes software that can be programmed by those of skill in the art to provide the described functionality.

The software can be represented as a sequence of binary bits maintained on a computer readable medium described above, for example, as memory device 70 in FIG. 2. The computer readable medium may include magnetic disks, optical disks, and any other volatile or (e.g., Random Access memory ("RAM")) non-volatile firmware (e.g., Read Only Memory ("ROM")) storage system readable by the processor. The memory locations where data bits are maintained also include physical locations that have particular electrical, magnetic, optical, or organic properties corresponding to the stored data bits. The software instructions are executed as data bits by the processor with a memory system causing a transformation of the electrical signal representation, and the maintenance of data bits at memory locations in the memory system to thereby reconfigure or otherwise alter the unit's operation. The executable software code may implement, for example, the methods as described above.

It should be understood that a hardware embodiment may take a variety of different forms. The hardware may be implemented as an integrated circuit with custom gate arrays or an application specific integrated circuit ("ASIC"). The embodiment may also be implemented with discrete hardware components and circuitry. In particular, it is understood that the logic structures and method steps described in the flow diagrams may be implemented in dedicated hardware such as an ASIC, or as program instructions carried out by a microprocessor or other computing device.

The claims should not be read as limited to the described order of elements unless stated to that effect. In addition, use of the term "means" in any claim is intended to invoke 35 U.S.C. §112, paragraph 6, and any claim without the word "means" is not so intended. Therefore, all embodiments that come within the scope and spirit of the following claims and equivalents thereto are claimed as the invention. This disclosure is intended to cover all variations, uses, or adaptations of the invention that generally follow the principles of the invention in the art to which it pertains.

The invention claimed is:

1. A method for detecting the presence of at least a first target analyte in a test spot, comprising:
    acquiring multiple images of a test spot and a control spot on a substrate having a plurality of spots containing specific binding complements to one or more target analytes, the multiple images being taken with different amounts of exposure time, wherein the test spot comprises metallic nanoparticles complexed to specific binding complements in the presence of at least a first target analyte, and wherein the control spot comprises metallic nanoparticles, with or without signal amplification, complexed to specific binding complements in the presence of at least a second target analyte;
    performing regression analysis on portions of the acquired multiple images of the test spot and the control spot using a processor so as to generate functions of an amount of exposure time versus intensity of the test spot and intensity of the control spot;
    selecting one of the different amounts of exposure time;
    using the generated functions to determine an intensity of the test spot at the selected amount of exposure time and an intensity of the control spot at the selected amount of exposure time; and
    determining the presence of metallic nanoparticle complexes in the test spot by comparing the intensity of the test spot with the intensity of the control spot at the selected amount of exposure time, wherein the presence of the metallic nanoparticle complexes in the test spot indicates presence of the at least a first target analyte in the test spot.

2. The method of claim 1, wherein the selected amount of exposure time is an optimal amount of exposure time that results in a predetermined level of saturation of at least a portion of an acquired image of the test spot and the control spot.

3. The method of claim 1, wherein determining the intensity of the test spot and intensity of the control spot at the selected amount of exposure time based on the functions generated comprises interpolating or extrapolating the functions generated.

4. The method of claim 3, wherein comparing the intensity of the test spot with the intensity of the control spot at the optimal exposure time comprises performing statistical analysis on the intensity of the test spot and the intensity of the control spot so as to determine if the intensity of the test spot is similar or dissimilar to the intensity of the control spot.

5. The method of claim 4, wherein performing the statistical analysis comprises performing differences between means testing.

6. The method of claim 1, wherein the test spot comprises a nucleic acid from a wildtype nucleic acid sequence, and wherein the control spot comprises a nucleic acid from a mutant nucleic acid sequence that is related to the wildtype nucleic acid sequence.

* * * * *